United States Patent [19]

Desai et al.

[11] Patent Number: 5,187,173

[45] Date of Patent: Feb. 16, 1993

[54] 2-SACCHARINYLMETHYL AND 4,5,6,7-TETRAHYDRO-2-SACCHARINYL-METHYL PHOSPHATES, PHOSPHONATES AND PHOSPHINATES USEFUL AS PROTEOLYTIC ENZYME INHIBITORS AND COMPOSITIONS AND METHOD OF USE THEREOF

[75] Inventors: Ranjit C. Desai; John J. Court, both of Colonie; Dennis J. Hlasta, Clifton Park; Chakrapani Subramanyam, East Greenbush, all of N.Y.

[73] Assignee: Sterling Winthrop Inc., New York, N.Y.

[21] Appl. No.: 814,741

[22] Filed: Dec. 27, 1991

[51] Int. Cl.$^5$ .................. A61K 31/425; C07D 275/06
[52] U.S. Cl. ...................................... 514/373; 548/113
[58] Field of Search ........................ 548/113; 514/373

[56] References Cited

U.S. PATENT DOCUMENTS

| | | | |
|---|---|---|---|
| 3,002,884 | 10/1961 | Lo | 167/33 |
| 3,314,960 | 4/1967 | Freed et al. | 260/281 |
| 4,195,023 | 3/1980 | Mulvey et al. | 548/209 |
| 4,263,393 | 4/1981 | Chen | 430/218 |
| 4,276,298 | 6/1981 | Jones et al. | 424/270 |
| 4,350,752 | 9/1982 | Reczek et al. | 430/219 |
| 4,363,865 | 12/1982 | Reczek et al. | 430/223 |
| 4,410,618 | 10/1983 | Vanmeter et al. | 430/219 |
| 4,547,371 | 10/1985 | Doherty et al. | 514/200 |
| 4,623,645 | 11/1986 | Doherty et al. | 514/200 |
| 4,659,855 | 4/1987 | Powers | 558/23 |

FOREIGN PATENT DOCUMENTS

| | | | |
|---|---|---|---|
| 1451417 | 9/1966 | France | 548/209 |
| 7200419 | 1/1972 | Japan | 514/373 |
| 0006496 | 1/1990 | Japan | 548/113 |
| WO9013549 | 11/1990 | PCT Int'l Appl. | 548/209 |

OTHER PUBLICATIONS

Chemical Abstracts 81, 22249n (1974) Chiyomaru et al.
Sunkel et al., J. Med. Chem. 31, 1886–1890 (1988).
Zimmerman et al., J. Biol. Chem. 255(20), 9848–9851 (1980).
Teshima et al., J. Biol. Chem., 257(9), 5085–5091 (1982).
Cha, Biochem. Pharmacol., 24, 2177–2185 (1975).
Powers et al., Biochem., 24, 2048–2058 (1985).
Svoboda et al., Coll. Czech. Chem. Commun., 51, 1133–1139 (1986).

*Primary Examiner*—Mary C. Lee
*Assistant Examiner*—Joseph K. McKane
*Attorney, Agent, or Firm*—Frederik W. Stonner; Paul E. Dupont

[57] ABSTRACT

4-$R_1$-$R_2$-$R_3$-2-Saccharinylmethyl, 4-$R_4$-4-$R_5$-6-$R_6$-4,5,6,7-tetrahydro-2-saccharinylmethyl and 4,7-C-4,5,6,7-tetrahydro-2-saccharinylmethyl phosphates, phosphonates and phosphinates of formulas I, II and IIA respectively herein, useful in the treatment of degenerative diseases, and compositions containing them, methods for using them to treat degenerative diseases, and processes for their preparation by reaction of the corresponding 2-halomethylsaccharins with a phosphate, phosphonate or phosphinic acid of formula III herein in the presence of an acid-acceptor.

9 Claims, No Drawings

2-SACCHARINYLMETHYL AND 4,5,6,7-TETRAHYDRO-2-SACCHARINYLMETHYL PHOSPHATES, PHOSPHONATES AND PHOSPHINATES USEFUL AS PROTEOLYTIC ENZYME INHIBITORS AND COMPOSITIONS AND METHOD OF USE THEREOF

BACKGROUND OF THE INVENTION (a) Field of the Invention

This invention relates to novel 2-saccharinylmethyl and 4,5,6,7-tetrahydro-2-saccharinylmethyl phosphates, phosphonates and phosphinates which inhibit the enzymatic activity of proteolytic enzymes, to compositions containing the same, to the method of use thereof in the treatment of degenerative diseases and to processes for their preparation.

(b) Information Disclosure Statement

The inhibition of proteolytic enzymes by nontoxic reagents is useful in the treatment of degenerative disorders, such as emphysema, rheumatoid arthritis and pancreatitis, in which proteolysis is a substantive element.

Protease inhibitors are widely utilized in biomedical research. Serine proteases are the most widely distributed class of proteolytic enzymes. Some serine proteases are characterized as chymotrypsin-like or elastase-like based upon their substrate specificity.

Chymotrypsin and chymotrypsin-like enzymes normally cleave peptide bonds in proteins at a site at which the amino acid residue on the carboxyl side is typically Trp, Tyr, Phe, Met, Leu or another amino acid residue which contains aromatic or large alkyl side chains.

Elastase and elastase-like enzymes normally cleave peptide bonds at a site at which the amino acid residue on the carboxyl side of the bond is typically Ala, Val, Ser, Leu or other similar, smaller amino acids.

Both chymotrypsin-like and elastase-like enzymes are found in leukocytes, mast cells and pancreatic juice in higher organisms, and are secreted by many types of bacteria, yeast and parasites.

Japanese Patent Publication 72/00419, published Jan. 7, 1972, discloses a number of 2-saccharinylmethyl benzoates, including 2-saccharinylmethyl benzoate per se and 2-saccharinylmethyl 2,4-dichlorobenzoate and 4-nitrobenzoate. The compounds are said to "have strong activity against rice blast, rice sheath blight, rice helminthosporium leaf spot and rice bacterial leaf blight disease".

Sunkel et al., J. Med. Chem., 31, 1886–1890 (1988) disclose a series of 2-saccharinyl-lower-alkyl-1,4-dihydropyridine-3-carboxylates having platelet aggregation inhibitory and anti-thrombotic activities.

Chen U.S. Pat. No. 4,263,393, patented Apr. 21, 1981, discloses various 2-aroylmethylsaccharins useful as "photographic elements and film units".

Mulvey et al. U.S. Pat. No. 4,195,023, patented Mar. 25, 1980, discloses $R_1$-2-$R_2$CO-1,2-benzisothiazol-3-ones, where $R_1$ is halogen, alkoxy, alkylamino, dialkylamino, alkoxycarbonyl, amino, nitro or hydrogen in the benzenoid ring and $R_2$ is hydrogen, alkyl, alkenyl, alkynyl, cycloalkyl, halophenyl, heteroaryl or substituted heteroaryl, and $R_1$-2-A-CO saccharins, where $R_1$ has the same meanings as the benzenoid ring substituents in the 1,2-benzisothiazol-3-ones and A is alkyl, alkenyl, alkynyl, cycloalkyl, fluorophenyl, heteroaryl or substituted-heteroaryl. The compounds are said to have elastase inhibitory activity and to be useful in the treatment of emphysema.

Zimmerman et al., J. Biol. Chem., 255(20), 9848–9851 (1980) disclose N-acylsaccharins, where the acyl group is furoyl, thenoyl, benzoyl, cyclopropanoyl, ethylbutyryl and acryloyl, having serine protease inhibitory activity.

Chemical Abstracts 81, 22249n (1974) discloses 4-methylphenyl 2-saccharinylcarboxylate which is said to have bactericidal and fungicidal activities.

Several classes of compounds are known to be serine protease inhibitors. For example Powers U.S. Pat. No. 4,659,855 discloses arylsulfonyl fluoride derivatives useful as elastase inhibitors. Doherty et al. U.S. Pat. Nos. 4,547,371 and 4,623,645 disclose cephalosporin sulfones and sulfoxides, respectively, which are stated to be potent elastase inhibitors useful in the treatment of inflammatory conditions, especially arthritis and emphysema.

Teshima et al., J. Biol. Chem., 257(9), 5085–5091 (1982) report the results of studies on serine proteases (human leukocyte elastase, porcine pancreatic elastase, cathepsin G and bovine chymotrypsin $A_\alpha$) with 4-nitrophenylesters and thioesters of N-trifluoroacetylanthranilates, 2-substituted-4H-3,1-benzoxazin-4-ones, 2-substituted-4-quinazolinones and 2-substituted-4-chloroquinazolines.

Cha, Biochem. Pharmacol., 24, 2177–2185 (1975) discusses kinetic approaches to the study of the binding of inhibitors to macromolecules, such as enzymes, and methods for determination of such parameters as the inhibition constants, reaction rates and bound and unbound enzyme concentrations.

Jones et al., U.S. Pat. No. 4,276,298 discloses 2-R-1,2-benzisothiazolinone-1,1-dioxides, where R is phenyl substituted by fluoro, dinitro, trifluoromethyl, cyano, alkoxycarbonyl, alkylcarbonyl, carboxyl, carbamoyl, alkylacylamino, alkylsulfonyl, N,N-dialkylsulfamoyl, trifluoromethoxy, trifluoromethylthio, trifluoromethylsulfonyl and trifluoromethylsulfinyl, or pyridyl substituted the same as R when R is phenyl except that pyridyl may also be mono-nitro substituted. The compounds are said to have protease enzyme inhibitory activity, especially elastase inhibitory activity, and to be useful in the treatment of emphysema, rheumatoid arthritis "and other inflammatory diseases".

Powers et al, Biochem., 24, 2048–2058 (1985) discloses studies of the inhibitions of four chymotrypsin-like enzymes, cathepsin G, rat mast cell proteases I and II, human skin chymase and chymotrypsin $A_{60}$, by N-furoylsaccharin and N-(2,4-dicyanophenyl)saccharin.

Svoboda et al., Coll. Czech. Chem. Commun., 51, 1133–1139 (1986) disclose the preparation of 4-hydroxy-2H-1,2-benzothiazine-3-carboxylates by intramolecular Dieckmann condensation of 2H-1,2-benzisothiazol-3-one-2-acetate-1,1-dioxide esters.

Reczek et al. U.S. Pat. Nos. 4,350,752 and 4,363,865 and Vanmeter et al. U.S. Pat. No. 4,410,618 relate to photographic reagents (Reczek U.S. Pat. No. 4,350,752 and Vanmeter et al.) and photographic dyes (Reczek U.S. Pat. No. 4,363,865) and disclose various 2-substituted-saccharins useful for such applications, for example "photographic reagents" bound through a heteroatom to an "imidomethyl blocking" group (Reczek U.S. Pat. No. 4,350,752), "carrier-diffusible photographic dyes" bound to the nitrogen atom of an imide through a 1,1-alkylene group (Reczek U.S. Pat. No. 4,363,865) and N-acylmethylimides which are described as "blocked photographic reagents" and which have a "residue of an organic photographic reagent containing a hetero atom through which it is bound to the blocking group" (Vanmeter).

Freed et al. U.S. Pat. No. 3,314,960 discloses 2-(1,1,3-trioxo-1,2-benzisothiazol-2-yl)glutarimides which are stated to be useful as sedatives.

2-Chloromethylsaccharin is disclosed in French Patent 1,451,417 as an intermediate for the preparation of N-methylsaccharin d,l-trans-chrysanthemate, useful as an insecticide, and Lo U.S. Pat. No. 3,002,884 discloses 2-chloro, 2-bromo and 2-iodomethylsaccharins, useful as fungicidal agents.

Dunlap et al. PCT application WO 90/13549, published Nov. 15, 1990, discloses a series of 2-substituted saccharin derivatives useful as proteolytic enzyme inhibitors.

SUMMARY OF THE INVENTION

In a composition of matter aspect, this invention relates to 4-$R_1$-$R_2$-$R_3$-2-saccharinylmethyl, 4-$R_4$-4-$R_5$-6-$R_6$-4,5,6,7-tetrahydro-2-saccharinylmethyl and 4,7-C-4,5,6,7-tetrahydro-2-saccharinylmethyl phosphates, phosphonates and phosphinates of formulas I, II and IIA respectively hereinbelow which have protease enzyme inhibitory activity and which are useful in the treatment of degenerative diseases.

In a composition aspect, the invention relates to compositions for the treatment of degenerative diseases which comprise a pharmaceutical carrier and an effective proteolytic enzyme inhibiting amount of a compound of formula I, II or IIA.

In a method aspect, the invention relates to a method of use of a compound of formula I, II or IIA in the treatment of degenerative diseases which comprises administering to a patient in need of such treatment a medicament containing an effective proteolytic enzyme inhibiting amount of the compound of formula I, II or IIA.

In a process aspect, the invention relates to a process for the preparation of a compound of formula I, II or IIA which comprises reacting a 4-$R_1$-$R_2$-$R_3$-2-halomethylsaccharin, a 4-$R_4$-4-$R_5$-6-$R_6$-4,5,6,7-tetrahydro-2-halomethylsaccharin or a 4,7-C-4,5,6,7-tetrahydro-2-halomethylsaccharin with a phosphate, phosphonate or phosphinic acid of formula III hereinbelow in the presence of an acid-acceptor.

DETAILED DESCRIPTION OF THE PREFERRED EMBODIMENTS

More specifically this invention relates to 4-$R_1$-$R_2$-$R_3$-2-saccharinylmethyl and 4-$R_4$-4-$R_5$-6-$R_6$-4,5,6,7-tetrahydro-2-saccharinylmethyl phosphates, phosphonates and phosphinates having the formulas:

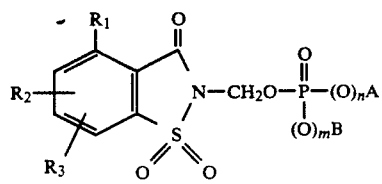

and

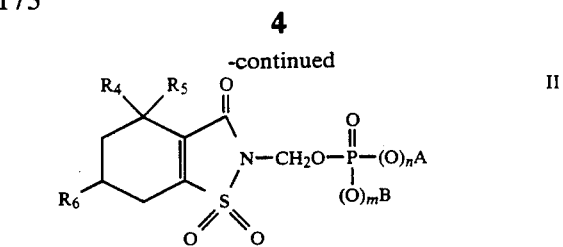

wherein:

$R_1$ is hydrogen, halogen, lower-alkyl, perfluoro-lower-alkyl, perchloro-lower-alkyl, lower-alkenyl, lower-alkynyl, cyano, amino, lower-alkylamino, di-lower-alkylamino, carboxamido, lower-alkoxy, benzyloxy, hydroxy, lower-alkoxycarbonyl or phenyl;

$R_2$ and $R_3$ are independently hydrogen or a substituent in any of the available 5-, 6- or 7-positions selected from the group consisting of halogen, cyano, nitro, N=B, 1-lower-alkyl-2-pyrrolyl, lower-alkylsulfonylamino, polyfluoro-lower-alkylsulfonylamino, polychloro-lower-alkylsulfonylamino, aminosulfonyl, lower-alkyl, polyfluoro-lower-alkyl, polychloro-lower-alkyl, cycloalkyl, lower-alkoxy, hydroxy, carboxy, carboxamido, hydroxy-lower-alkyl, formyl, aminomethyl, polyfluoro-lower-alkylsulfonyl, polychloro-lower-alkylsulfonyl, lower-alkylsulfonylaminosulfonyl, lower-alkoxy-poly-lower-alkyleneoxy, cycloalkyloxy, hydroxy-lower-alkoxy, polyhydroxyalkoxy, or acetal or ketal thereof, polyalkoxyalkoxy, (lower-alkoxy)$_2$-P(O)O—, —SR, —SOR, —SO$_2$R, —OCOR, —O—($C_{1-10}$-alkylene)—COOR, —O—($C_{1-10}$-alkylene)—COOH and —O—($C_{2-10}$-alkylene)—N=B, where R is lower-alkyl, phenyl, benzyl or naphthyl, or phenyl or naphthyl substituted by from one to two substituents selected from lower-alkyl, lower-alkoxy or halogen, and —N=B in each instance is amino, lower-alkylamino, di-lower-alkylamino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, 1-imidazolyl or (carboxy-lower-alkyl)amino; or $R_2$ and $R_3$ together represent a 3-atom or 4-atom unsubstituted or methylated saturated bridge bridging the carbon atoms at the 5,6 or 6,7 positions, wherein the atoms of the bridge consist of one or two carbon atoms and two of the same or different heteroatoms selected from the group consisting of oxygen, sulfur and nitrogen;

$R_4$ is hydrogen, lower-alkyl or phenyl;

$R_5$ is hydrogen or primary lower-alkyl;

or $R_4$ and $R_5$, taken together, represent ethylene;

$R_6$ is hydrogen or lower-alkoxy;

m and n are independently 0 or 1;

when m and n are 1, A and B are independently hydrogen, lower-alkyl, phenyl, lower-alkoxyphenyl or benzyl, or, taken together, represent:

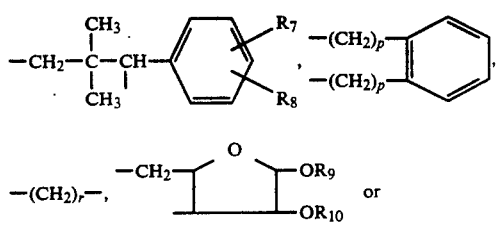

-continued

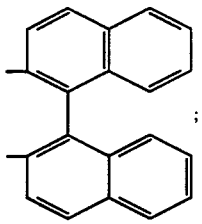

where $R_7$ and $R_8$ are independently hydrogen or chlorine, $R_9$ and $R_{10}$ each is hydrogen or together represent isopropylidene, p is 0 or 1 and r is 2, 3 or 4;

when m is 1 and n is 0, A and B are independently lower-alkyl, phenyl, benzyl or 2-pyridinyl; and when m and n are 0, A and B are independently lower-alkyl, phenyl or lower-alkoxyphenyl.

The invention also relates to compounds of the formula:

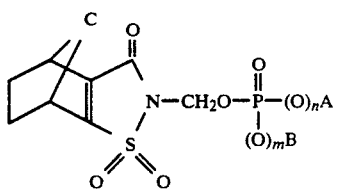

IIA wherein C is methylene, ethylene or dimethylmethylene and A, B, m and n have the meaning defined hereinbefore for formulas I and II.

Preferred compounds of formula I are those wherein:

$R_1$ is hydrogen, lower-alkyl, especially $C_{1-4}$ lower-alkyl and more especially propyl, isopropyl or sec-butyl, or lower-alkoxy, especially methoxy or ethoxy;

$R_2$ is lower-alkoxy, especially $C_{1-3}$ lower-alkoxy and more especially methoxy or isopropoxy, polyalkoxyalkoxy, especially 2,3-dimethoxypropoxy, lower-alkoxy-poly-lower-alkyleneoxy, especially methoxy-lower-alkyleneoxyethoxy, or polyhydroxyalkoxy, or ketal or acetal thereof, especially dihydroxyalkoxy, or ketal or acetal thereof, and more especially 2,3-dihydroxypropoxy, or dimethyl ketal thereof;

$R_3$ is hydrogen or lower-alkoxy, especially methoxy; m and n both are 0 or 1;

when m and n are 1, A and B are independently hydrogen, lower-alkyl, phenyl, lower-alkoxyphenyl or benzyl; and when m and n are 0, A and B are independently lower-alkyl, phenyl or lower-alkoxyphenyl.

Other preferred compounds of formula I are those wherein:

$R_1$ is hydrogen, lower-alkyl, especially $C_{1-4}$ lower-alkyl and more especially isopropyl or sec-butyl, or lower-alkoxy, especially methoxy or ethoxy;

$R_2$ is hydrogen, hydroxy or lower-alkoxy, especially methoxy or ethoxy, or polyhydroxyalkoxy, or ketal or acetal thereof, especially dihydroxyalkoxy, or ketal or acetal thereof, more especially 2,3-dihydroxypropoxy, or dimethyl ketal thereof;

$R_3$ is hydrogen;

m and n both are 0 or 1;

when m and n are 1, A and B are independently, especially both, hydrogen, lower-alkyl, especially $C_{1-4}$ lower-alkyl and more especially methyl, ethyl, isopropyl or butyl, phenyl, lower-alkoxyphenyl or benzyl; and when m and n are 0, A and B are independently, especially both, lower-alkyl, especially $C_{1-4}$ lower-alkyl and more especially butyl, phenyl or lower-alkoxyphenyl, especially methoxyphenyl and more especially 4-methoxyphenyl.

Preferred compounds of formula II are those wherein:

$R_4$ is hydrogen or lower-alkyl, especially methyl, ethyl or isopropyl, more especially methyl;

$R_5$ is hydrogen or methyl;

$R_6$ is hydrogen or lower-alkoxy;

m and n are both 0 or 1;

when m and n are 1, A and B are independently hydrogen, lower-alkyl, phenyl or benzyl; and when m and n are 0, A and B are independently lower-alkyl, phenyl or lower-alkoxyphenyl.

Other preferred compounds of formula II are those wherein:

$R_4$ is lower-alkyl, especially methyl;

$R_5$ is primary lower-alkyl, especially methyl;

$R_6$ is hydrogen or lower-alkoxy, especially hydrogen;

m and n both are 0 or 1, especially 1;

A and B are independently, especially both, lower-alkyl, especially $C_{1-4}$ lower-alkyl.

It should be understood that the compounds having the general structural formulas I and II are usually named in the chemical literature as 1,2-benzisothiazol-3(2H)-one 1,1-dioxides. However for the sake of brevity, such compounds are frequently named as saccharin derivatives, and that nomenclature will be used hereinafter in describing the compounds of the invention and their biological properties.

As used herein the terms lower-alkyl, lower-alkoxy and lower-alkane mean monovalent aliphatic radicals, including branched chain radicals, of from one to ten carbon atoms. Thus the lower-alkyl (or lower-alkane) moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein the terms cycloalkyl and cycloalkyloxy mean such radicals having from three to seven carbon atoms illustrated by cyclopropyl, cyclobutyl, cyclopentyl, cyclohexyl, cycloheptyl, cyclopropyloxy, cyclobutyloxy, cyclopentyloxy and cycloheptyloxy.

As used herein the term halogen (or halo) means fluorine, chlorine, bromine or iodine.

As used herein the terms lower-alkenyl and lower-alkynyl mean monovalent, unsaturated radicals, including branched chain radicals, of from two to ten carbon atoms and thus include 1-ethenyl, 1-(2-propenyl), 1-(2butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl), and the like.

As used herein, the term $C_{2-10}$-alkylene means divalent, saturated radicals, including branched chain radicals, of from two to ten carbon atoms having their free valences on different carbon atoms; and the term $C_{1-10}$-alkylene means divalent, saturated radicals, including branched chain radicals, of from one to ten carbon atoms having their free valences on the same or different carbon atoms. Such terms thus include 1,2-ethylene, 1,3-propylene, 1,4-butylene, 1-methyl-1,2-ethylene, 1,8-octylene and the like and in the case only of $C_{1-10}$, also methylene, ethylidene, propylidene and the like.

As used herein, the term lower-alkoxy-poly-lower-alkyleneoxy means such radicals in which lower-alkoxy has the meaning given above, poly means 2 to 4, and lower-alkylene in lower-alkyleneoxy means divalent saturated radicals, including branched radicals, of from two to five carbon atoms. That term thus includes $CH_3(OCH_2CH_2)_pO-$, $CH_3CH_2[OCH_2CH(CH_3]_pO-$. where p=2-4, and the like.

As used herein, hydroxy-lower-alkoxy means lower-alkoxy as defined above substituted by a hydroxy group other than on the C-1 carbon atom and thus includes 2-hydroxyethoxy and the like.

As used herein, the term polyhydroxyalkoxy means such a group wherein alkoxy is a monovalent aliphatic radical of from two to five carbon atoms substituted by from two or four hydroxy groups none of which are attached to the same or the C-1 carbon atom and thus includes 2,3-dihydroxypropoxy, 2,3,4,5-tetrahydroxypentoxy and the like.

As used herein, the term polyalkoxyalkoxy means monovalent aliphatic alkoxy radicals of from three to five carbon atoms substituted by from two to four methoxy or ethoxy groups none of which are attached to the same or the C-1 carbon atom.

The compounds of the present invention inhibit the activity of serine proteases, specifically human leukocyte elastase and the chymotrypsin-like enzymes, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigous and alpha-1-antitrypsin deficiency.

The compounds of formulas I, II and IIA are prepared by reaction of a 4-$R_1$-$R_2$-$R_3$-2-halomethylsaccharin, 4-$R_4$-4-$R_5$-6-$R_6$-4,5,6,7-tetrahydro-2-halomethylsaccharin or 4,7-C-4,5,6,7-tetrahydro-2-halomethylsaccharin respectively with an appropriate phosphoric acid di-ester, phosphonic acid mono-ester or phosphinic acid of the formula

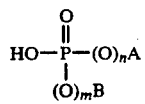

where A, B, m and n have the meanings given hereinabove except that when m and n are 1, A and B are other than hydrogen. The reaction can be carried out in the presence of an acid-acceptor, such as an alkali metal carbonate, a tri-lower-alkylamine or 1,8-diazabicyclo[5.4.0]undec-7-ene, hereinafter DBU. The reaction is carried out in an organic solvent inert under the conditions of the reaction, for example acetone, methyl ethyl ketone (MEK), acetonitrile, tetrahydrofuran (THF), diethyl ether, dimethylformamide (DMF), N-methylpyrrolidinone, methylene dichloride (MDC), xylene, toluene or lower-alkanols, at a temperature in the range from ambient up to the boiling point of the solvent used.

The compounds of formulas I, II and IIA wherein m and n are 1 and A and B are hydrogen are prepared by hydrogenolysis of the corresponding compounds wherein m and n are 1 and A and B are benzyl.

The 4-$R_1$-$R_2$-$R_3$-2-halomethylsaccharins required for the preparation of the compounds of formula I are prepared by the methods described by D'Alelio et al., J. Macromol. Sci-Chem., A3(5), 941 (1969) and Saari et al., J. Het. Chem., 23, 1253 (1986). In the method described by Saari, a methyl ester of an appropriate anthranilic acid is prepared by conventional means from the substituted anthranilic acid and the ester diazotized. The diazonium salt is then reacted with sulfur dioxide and cupric chloride to produce a sulfonyl chloride which is then reacted with concentrated ammonium hydroxide to produce the substituted saccharin derivatives of formula IV. The latter, on reaction with formaldehyde in a lower-alkanol solvent, affords the 4-$R_1$-$R_2$-$R_3$-2-hydroxymethylsaccharins of formula V, which, on reaction with a thionyl halide or a phosphorus trihalide, afford the corresponding 4-$R_1$-$R_2$-$R_3$-2-halomethylsaccharin derivatives of formula VI.

The 4-$R_1$-$R_2$-$R_3$-2-halomethylsaccharins of formula VI, where $R_1$, $R_2$, $R_3$ have the meanings given above and X is chlorine or bromine, can also be prepared by reaction of a corresponding 4-$R_1$-$R_2$-$R_3$-2-phenylthiomethylsaccharin with a sulfuryl halide in an inert organic solvent, for example MDC, ethylene dichloride (EDC) or carbon tetrachloride, at a temperature from around 0° C. to around 30° C. The 4-$R_1$-$R_2$-$R_3$-2-phenylthiomethylsaccharins are in turn prepared by reaction of a 4-$R_1$-$R_2$-$R_3$-saccharin of formula IV with a halomethylphenyl sulfide in an inert organic solvent, such as toluene, xylene, DMF or MDC at a temperature in the range from ambient up to the boiling point of the solvent used. The reaction can be carried out by reaction of the halomethyl phenyl sulfide with either the thallium salt of the saccharin derivative of formula IV (prepared by reaction of the saccharin derivative with a thallium lower-alkoxide in a lower-alkanol); or with a di-lower-alkyl ammonium salt of the saccharin derivative (prepared as described below) in the presence of a tetra-lower-alkyl ammonium halide, such as tetrabutyl ammonium bromide (hereinafter TBAB); or with the saccharin derivative of formula IV per se in the presence of a tetra-lower-alkyl ammonium halide; or with the saccharin derivative of formula IV per se in the presence of a tetra-lower-alkyl ammonium halide and an alkali metal lower-alkoxide, such as potassium t-butoxide.

The saccharins of formula IV may also be converted to the chloromethyl saccharins of formula VI, wherein X is Cl, in one step by reaction with an excess of formaldehyde or a formaldehyde equivalent, such as paraformaldehyde or 1,3,5-trioxane, and a chlorosilane, preferably chlorotrimethylsilane, in the presence of a Lewis acid, preferably a catalytic amount of stannic chloride, in an inert solvent, preferably 1,2-dichloroethane (ethylene dichloride, EDC).

These approaches are illustrated as follows, where $R_1$, $R_2$ and $R_3$ have the meanings given above, Alk is lower-alkyl, X is halogen and Ph is phenyl

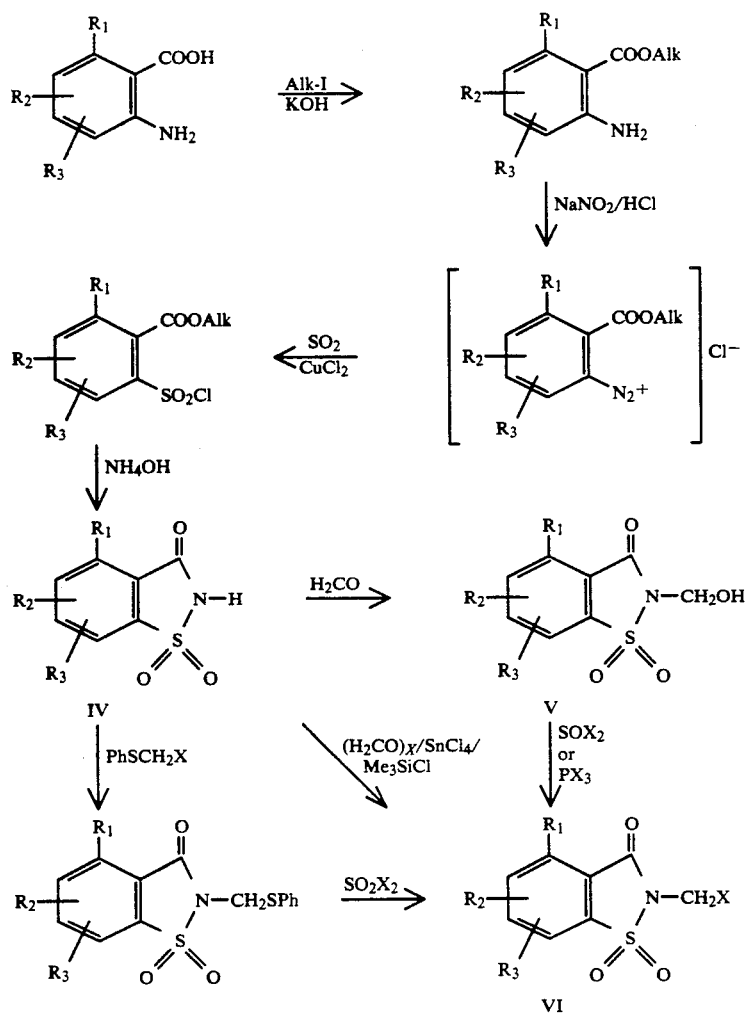

The compounds of formula IV can also be prepared by reaction of a 2-$R_1$-$R_2$-$R_3$-N,N-di-lower-alkylbenzamide of formula VII with one molar equivalent of a lower-alkyl alkali metal, such as lithium, optionally in the presence of a tetra-lower-alkylethylenediamine in an inert organic solvent, for example THF, and reaction of the resulting alkali metal salt either with sulfur dioxide at a temperature in the range from $-50°$ C. to $-80°$ C. followed by reaction of the resulting alkali metal sulfinate with hydroxylamine-O-sulfonic acid in the presence of aqueous base, or with a sulfuryl halide followed by ammonia. When the sulfur dioxide-hydroxylamine-O-sulfonic acid route is used, it is particularly advantageous to neutralize the hydroxylamine-O-sulfonic acid with one equivalent of aqueous sodium hydroxide prior to addition of the alkali metal sulfinate. The resulting 2-$R_1$-$R_2$-$R_3$-6-aminosulfonyl-N,N-di-lower-alkylbenzamide is thereafter heated in an acid medium to effect cyclization of the latter to produce the di-lower-alkyl ammonium salt of the desired 2-$R_1$-$R_2$-$R_3$-saccharin of formula IV, which can be used as such in the subsequent reaction or, if desired, can be hydrolyzed in dilute acid and the free saccharin isolated. It is preferred to carry out the cyclization in refluxing glacial acetic acid. The method is illustrated as follows where $R_1$, $R_2$, $R_3$ and Alk have the meanings given above, and the alkali metal is lithium.

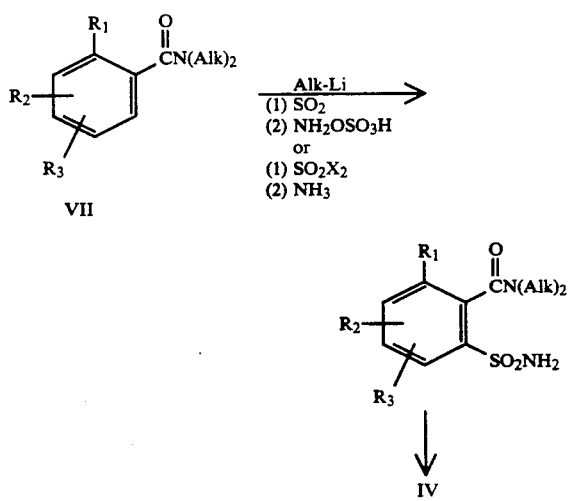

The compounds of formula IV where $R_1$ is either primary or secondary lower-alkyl, and which are useful as intermediates for the preparation of the compounds of formula I as described above, are prepared by one of the following methods.

The compounds of formula IV where $R_1$ is primary lower-alkyl are prepared by reacting a 4-methyl-$R_2$-$R_3$-saccharin (formula IV, $R_1$ is $CH_3$) with two molar equivalents of a lower-alkyl lithium in an inert organic solvent, for example THF, and reacting the resulting lithium salt with one molar equivalent of a lower-alkyl halide, both reactions being carried out at a temperature in the range from about $-50°$ C. to $-80°$ C.

The compounds of formula IV where $R_1$ is primary lower-alkyl and $R_2$ and $R_3$ are other than hydrogen, or $R_1$ is secondary lower-alkyl and $R_2$ and $R_3$ are as defined for formula I comprises reaction of a 2-primary-lower-alkyl-$R_2$-$R_3$-N,N-di-lower-alkylbenzamide (formula VII, $R_1$ is primary-lower-alkyl) with one molar equivalent of either a lower-alkyl lithium in the presence of a tetra-lower-alkylethylenediamine or a lithium di-lower-alkylamide, optionally in the presence of a tetra-lower-alkylethylenediamine, in an inert organic solvent, for example THF, and reaction of the resulting lithium salt with one molar equivalent of a lower-alkyl halide at a temperature in the range from about $-50°$ C. to $-80°$ C. The resulting 2-primary or secondary-lower-alkyl-$R_2$-$R_3$-N,N-di-lower-alkylbenzamide is thereafter converted to the compounds of formula IV, where $R_1$ is primary or secondary lower-alkyl, by the same sequence of reactions described above, i.e., by reaction of the 2-primary or secondary-lower-alkyl-$R_2$-$R_3$-N,N-di-lower-alkylbenzamide with one molar equivalent of a lower-alkyl lithium; reaction of the resulting lithium salt either with sulfur dioxide followed by hydroxylamine-O-sulfonic acid in the presence of base or with a sulfuryl halide followed by ammonia; and cyclization of the product to the desired 4-primary or secondary-lower-alkyl-$R_2$-$R_3$-saccharin of formula IV.

When the 2-lower-alkyl group in the 2-lower-alkyl-$R_2$-$R_3$-N,N-di-lower-alkylbenzamide starting material is methyl, alkylation affords species where the 2-lower-alkyl group is either straight or branched depending upon whether a straight or branched chain lower-alkyl halide is used for the alkylation. On the other hand, when the 2-lower-alkyl group in the starting material contains more than one carbon atom, alkylation takes place on the carbon atom adjacent the benzene ring and affords products having a sec.-lower-alkyl group at the 2-position.

A particularly useful method for the preparation of compounds IV where $R_1$ is n-lower-alkyl and $R_2$ and $R_3$ are hydrogen involves the protection of the benzylic protons of the starting material VII with a trialkylsilyl group, thereby permitting lithiation at the 6-position and formation of the sulfonamide as described above. This approach is illustrated as follows wherein $R_{11}$-$CH_2$ is n-lower-alkyl.

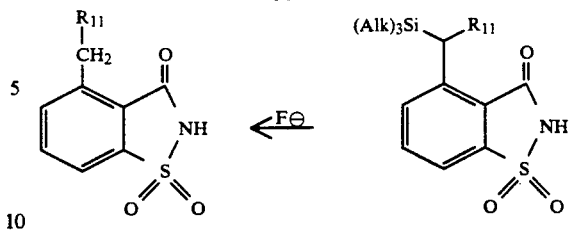

A 2-n-lower-alkylbenzamide is silylated by forming the benzylic anion using an alkyl lithium or, preferably, a lithium dialkylamide (LDA) in an inert solvent, preferably THF, and treating with a suitable chlorotrialkylsilane, preferably chlorotrimethylsilane. The saccharin is synthesized as before, and the silyl group is removed by treatment with a source of fluoride anion, preferably cesium fluoride in DMF or tetra-n-butylammonium fluoride in an inert solvent.

Access to certain of the required saccharin and tetrahydrosaccharin intermediates in some cases requires building up the two rings making up the saccharin nucleus. Thus to prepare saccharins of formula IV where $R_1$ is lower-alkoxy, $R_2$ is 7-hydroxy and $R_3$ is hydrogen, 3,3-dithiobispropionic acid is converted to the bis acid chloride by reaction of the acid with thionyl chloride, and the acid chloride is then reacted with two molar equivalents of benzylamine to produce the bis N-benzylamide. The latter, on reaction with sulfuryl chloride in an organic solvent, such as MDC, EDC or carbon tetrachloride, affords 5-chloro-2-benzyl-2H-isothiazol-3-one, which is oxidized with one molar equivalent of a peracid, such as perbenzoic acid or 3-chloroperbenzoic acid, to 5-chloro-2-benzyl-3(2H)-isothiazolone 1-oxide. The latter, on heating under pressure with a 2-lower-alkoxyfuran in an organic solvent, such as benzene, toluene or xylene, affords a 4-lower-alkoxy-7-hydroxy-2-benzyl-1,2-benzisothiazol-3(2H)-one 1-oxide. The 7-hydroxy group can, if desired, then be reacted with a lower-alkyl halide or a lower-alkyl-(O-lower-alkylene)$_p$-halide, where halide is bromide, chloride or iodide, to give the corresponding 4,7-di-lower-alkoxy or 4-lower-alkoxy-7-[lower-alkyl-(O-lower-alkylene)$_p$-O]-2-benzyl-1,2-benzisothiazol-3(2H)-one 1-oxide. Further oxidation of the product with one molar equivalent of a peracid as described above followed by catalytic debenzylation affords the corresponding 4-lower-alkoxy-7-hydroxysaccharins. The method is illustrated as follows where Bz is benzyl:

$$\text{(-SCH}_2\text{CH}_2\text{COOH)}_2 \xrightarrow[\text{BzNH}_2]{\text{SOCl}_2} \text{(-SCH}_2\text{CH}_2\text{CONHBz)}_2$$

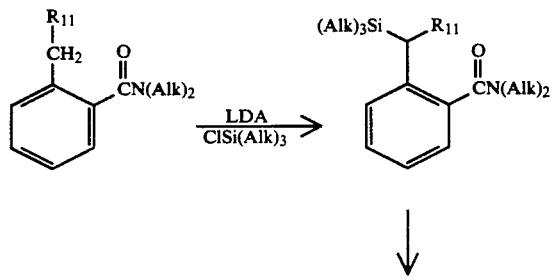

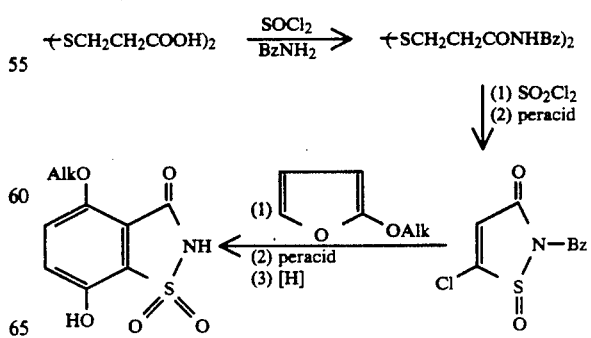

When the 4,5,6,7-tetrahydrosaccharin of formula VIII is desired, the following modification is used:

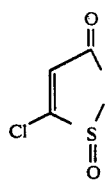

halomethyl derivative by the procedures described hereinbefore for the preparation of compound VI from compound IV.

Compounds of formula I wherein $R_1$ is lower-alkyl or phenyl and $R_2$ and $R_3$ are hydrogen may be synthesized by an alternate route from 2-cyclohexenone:

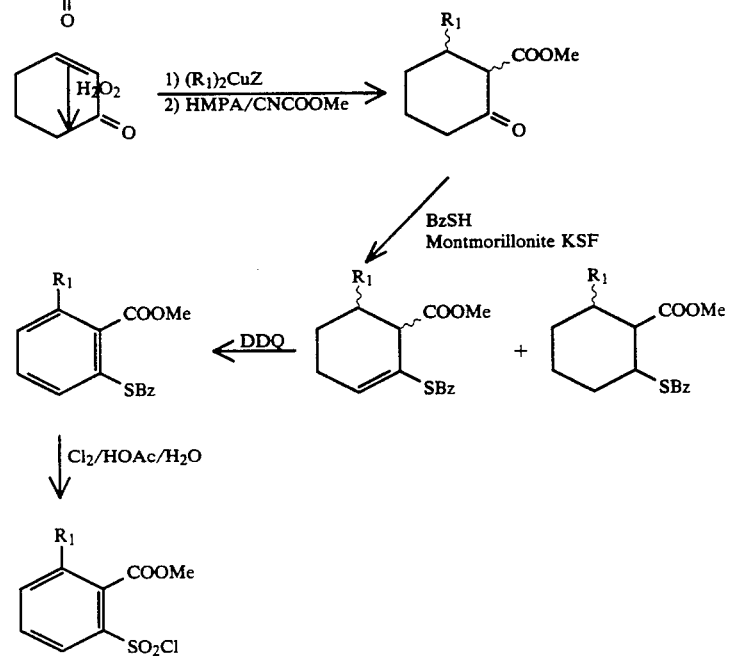

2-Cyclohexenone is reacted with the cuprate $(R_1)_2CuZ$, where Z is lithium or $Mg(X')_2$, where X' is bromide, chloride or iodide, followed by methyl cyanoformate according to the method of Winkler et al. [*Tet. Lett.* 1987, 1051 and *J. Org. Chem.* 54, 4491 (1989)]. The resulting β-ketoester is reacted with benzylmercaptan in the presence of the acidic clay Montmorillonite KSF to produce a mixture of regioisomers of the benzylthioenol ether. The mixture is aromatized by treatment with dichlorodicyanobenzoquinone (DDQ) and oxidized with chlorine gas in aqueous acid to provide the sulfonyl chloride ester, which may then be converted to the corresponding intermediate VI as shown earlier.

The 4,5,6,7-tetrahydrosaccharins which are the starting materials for the compounds of formula II where $R_6$ is hydrogen are synthesized by a route similar to the preceding one:

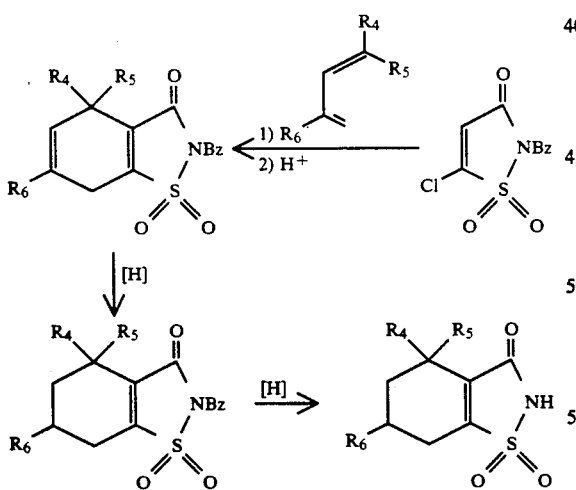

VIII

The 5-chloro-2-benzyl-2H-isothiazole-3-one 1-oxide may be oxidized with a suitable oxidizing agent, preferably hydrogen peroxide in acetic acid, to the 1,1-dioxide which is then reacted under typical Diels Alder conditions with the appropriate diene and reduced to provide the 2-benzyl tetrahydrosaccharin which is hydrogenolyzed as before to the tetrahydrosaccharin VIII, which may then be converted to the intermediate 2-

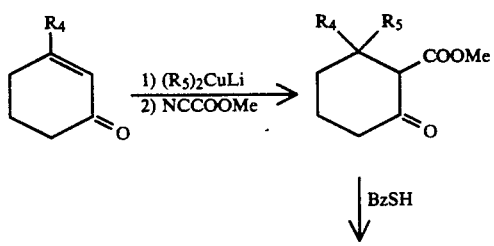

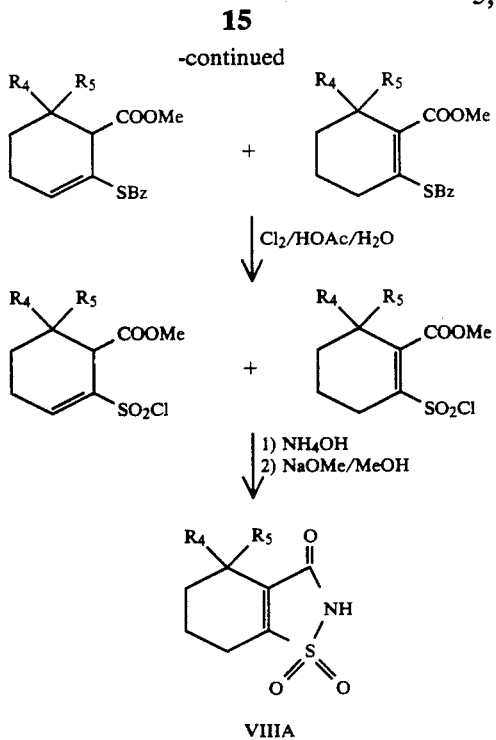

VIIIA

A 3-lower-alkyl-2-cyclohexenone is reacted with the appropriate di-(lower-alkyl) lithium cuprate in an ethereal solvent, preferably diethyl ether, at −50° to +20° C., preferably about 0° C., and the resulting adduct is treated in situ with methyl cyanoformate and hexamethylphosphoramide. The 6,6-di-(lower-alkyl)-2-oxocyclohexane carboxylate so produced is reacted with benzyl mercaptan as described above and the mixture of 2-(benzylthio)cyclohexene carboxylates is oxidatively chlorinated as described above to provide a mixture of chlorosulfonyl esters that are treated with ammonia as before to yield the desired 4,4-di-(lower-alkyl)-4,5,6,7-tetrahydrosaccharin VIIIA, which may then be converted to the intermediate 2-halomethyl derivative as described hereinbefore.

It will be appreciated that each of the conversions of saccharin IV to 2-halomethylsaccharin VI described herein are equally applicable to the conversion of tetrahydrosaccharins VIII and VIIIA to the corresponding 2-halomethyltetrahydrosaccharins.

The phosphates, phosphonates and phosphinic acids of formula III belong to well known classes of phosphorus compounds. References disclosing such classes of phosphorus compounds and methods for their preparation are numerous, for example, M. Regitz, Organische Phosphor-Verbindungen I and II, Hauben-Weyl, Methoden Der Organischen Chemie, Vierte Auflage, Erweiterungs-Und-Folge-Bande, Bande E1 and E2, Georg Thieme Verlag Stuttgart.New York, 1982; Robert Engel, Ph.D., Synthesis of Carbon-Phosphorus Bonds, CRC Press, Inc., Boca Raton, Fla., 1988; J. Jankowska et al., Synthesis (1984), 408; K. Nagasawa, Chem, and Pharm. Bull. 7, 397 (1959); and J. G. Moffatt et al., J. Am. Chem. Soc. 79, 1194 (1957).

Simple chemical transformations which are conventional and well known to those skilled in the art of chemistry can be used for effecting changes in functional groups in the compounds of the invention. For example, catalytic reduction of nitro groups to produce the corresponding amino substituted compounds, oxidation of sulfides or sulfoxides to prepare the corresponding, respective sulfoxides or sulfones, saponification of esters to produce corresponding carboxylic acids, catalytic debenzylation of phenolic ethers, benzylamines or benzyl phosphates to produce the corresponding phenols, debenzylated amines and debenzylated phosphates, or reaction of phenols with an alkylating agent in the presence of base or an alcohol in the presence of a coupling agent to produce ethers as desired can be carried out.

In standard biological test procedures, representative examples of compounds of the invention have been found to possess human leukocyte elastase (HLE) inhibitory activity, and are thus useful in the treatment of degenerative diseases, such as emphysema, rheumatoid arthritis, pancreatitis, cystic fibrosis, chronic bronchitis, adult respiratory distress syndrome, inflammatory bowel disease, psoriasis, bullous pemphigous and alpha-1-antitrypsin deficiency.

The compounds of the invention having basic functions can be converted to the acid-addition salt form by interaction of the base with an acid. In like manner, the free base can be regenerated from the acid-addition salt form in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the bases and all of their acid-addition salts are readily interconvertible.

Likewise compounds of the invention having acid, i.e., carboxylic acid and phosphate, functions can be converted to salt forms thereof by reaction of the acid or phosphate with a base, such as alkali metal or ammonium hydroxides or with organic bases such as alkyl, dialkyl or trialkylamines, and the acids and phosphates can be regenerated from the salts by treatment of the salts with aqueous acids.

The compounds of the invention and their salts have inherent pharmacological activity of a type to be more fully described hereinbelow. This inherent pharmacological activity can be enjoyed in useful form for pharmaceutical purposes by employing the free bases or free acids themselves or the salts formed from pharmaceutically acceptable acids and bases; that is, acids or bases whose anions or cations are innocuous to the animal organism in effective doses of the salts so that beneficial properties inherent in the common structural entity represented by the free bases and free acids are not vitiated by side effects ascribable to the anions or cations.

In utilizing this pharmacological activity of the salt, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base or aqueous acid as explained above, or alternatively they can be converted to any desired pharmaceutically acceptable salt by double decomposition reactions involving the anion or cation, for example by ion-exchange procedures.

Moreover, apart from their usefulness in pharmaceutical applications, the salts are useful as characterizing or identifying derivatives of the free bases or free acids or in isolation or purification procedures. Like all of the salts, such characterization or purification salt derivatives can, if desired, be used to regenerate the pharmaceutically acceptable free bases or free acids by reaction of the salts with aqueous base or aqueous acid, or alternatively they can be converted to a pharmaceutically acceptable salt by, for example, ion-exchange procedures.

The novel feature of the compounds then resides in the concept of the free bases and acids and the cationic and anionic forms of those compounds having basic and/or acid functions and not in any particular acid or base moiety or acid anion or base cation associated with the salt forms of the compounds; rather, the acid or base moieties or the anions or cations which can be associated with the salt forms are in themselves neither novel nor critical and therefore can be any acid anion or base cation capable of salt formation with the bases or acids.

The compounds of the invention can be prepared for pharmaceutical use by incorporating them in unit dosage form as tablets or capsules for oral administration either alone or in combination with suitable adjuvants such as calcium carbonate, starch, lactose, talc, magnesium stearate, gum acacia and the like. Still further, the compounds can be formulated for oral, parenteral or aerosol inhalation administration either in aqueous solutions of water soluble salts of the compounds or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

The molecular structures of the compounds of the invention were assigned on the basis of study of their infrared and NMR spectra. The structures were confirmed by the correspondence between calculated and found values for elementary analyses for the elements.

The following examples will further illustrate the invention without, however, limiting it thereto. All melting points are uncorrected.

PREPARATION OF STARTING MATERIALS

PREPARATION 1

Powdered potassium hydroxide (7.4 g, 0.132 mol) was admixed with dimethyl sulfoxide (DMSO) (100 ml), and the mixture was stirred for 5 minutes. 6-Methylanthranilic acid (10.0 g, 0.066 mol) was then added to the mixture and iodomethane (4.52 ml, 0.073 mol) added dropwise. The reaction mixture was stirred for 30 minutes at room temperature, then diluted with 250 ml of ether, washed with water (3×100 ml), dried over magnesium sulfate and concentrated. The crude product was filtered through a pad of flash grade (32–63) silica gel and eluted with 1:9 ether:hexane to afford 4.23 g (39%) of methyl 6-methylanthranilate as an oil.

The methyl 6-methylanthranilate so prepared (4.23 g, 0.026 mol) was dissolved in 25 ml of acetic acid and the solution cooled to 0° C. Concentrated hydrochloric acid (45 ml) was added to produce a tan slurry. A solution of 1.89 g (0.027 mol) of sodium nitrite in 8 ml water was added dropwise with stirring, the resulting orange solution was stirred at 0° C. for 1 hour and then added in 6 portions to a mixture of 2.18 g (0.013 mol) of cupric chloride dihydrate and sulfur dioxide (6.3 g) in 33 ml of acetic acid and 6 ml of water at 0° C. The dark green solution was stirred at room temperature overnight, poured into 300 ml of ice-water, and the solid which separated was collected and dried by suction to provide 1.11 g of methyl 2-chlorosulfonyl-6-methylbenzoate which was immediately added to 100 ml of ice cold ammonium hydroxide and stirred at room temperature overnight. The solution was acidified to pH 1 with concentrated hydrochloric acid, and the resulting precipitate was collected and air-dried to provide 729 mg (12%) of 4-methylsaccharin, mp 224°–226° C.

A mixture of 1.0 g (0.005 mol) of 4-methylsaccharin, 0.33 g (0.001 mol) of TBAB and 1.2 g (0.0075 mol) of chloromethyl phenyl sulfide in 25 ml of toluene was heated under reflux for about sixteen hours and then cooled, diluted with ethyl acetate and the solution washed with aqueous bicarbonate and water. The organic layer was dried and taken to dryness to give 0.74 g of 2-phenylthiomethyl-4-methylsaccharin.

The latter (0.74 g, 0.002 mol) was dissolved in 25 ml of MDC and the solution treated dropwise over a period of about two hours with stirring with a solution of 0.47 g (0.003 mol) of sulfuryl chloride in MDC and the reaction mixture taken to dryness. The yellow residual solid was triturated with hexane and filtered and dried to give 0.46 g of 2-chloromethyl-4-methylsaccharin as a pale yellow solid.

PREPARATION 2

Using the procedure described above in Preparation 1, 5.0 g (0.029 mol) of 6-chloroanthranilic acid and 2.75 ml (0.044 mol) of iodomethane were reacted in the presence of 4.08 g (0.073 mol) of powdered potassium hydroxide to give 4.22 g (78%) of methyl 6-chloroanthranilate as an oil.

4-Chlorosaccharin was prepared by the same method as used for the preparation of 4-methylsaccharin using 4.22 g (0.023 mol) of methyl 6-chloroanthranilate in 22 ml of acetic acid and 40 ml of concentrated hydrochloric acid and 1.68 g (0.024 mol) of sodium nitrite in 7 ml of water to prepare the diazonium salt which was added to 1.93 g (0.011 mol) of cupric chloride dihydrate and 6.5 g of sulfur dioxide in 30 ml of acetic acid and 5 ml of water. The resulting methyl 2-chlorosulfonyl-6-chlorobenzoate was treated with 150 ml of ammonium hydroxide as described above to afford 3.07 g (62%) of 4-chlorosaccharin as a pale yellow solid, mp 245°–246° C.

2-Hydroxymethyl-4-chlorosaccharin was prepared by heating a solution of 1.00 g (0.0046 mol) of 4-chlorosaccharin and 3.22 ml of aqueous 37% formalin in ethanol. All attempts to crystallize the viscous oily product resulted in decomposition to the starting material, and the product was thus used in the next step without characterization.

The crude 2-hydroxymethyl-4-chlorosaccharin so prepared (609 mg, 0.0025 mol) was admixed with 5 ml of diethyl ether, and 3 ml of thionyl chloride was added. The resulting mixture was heated to effect complete solution, stirred at room temperature overnight, diluted with 20 ml of ether and filtered through a pad of celite topped with sand and eluted with ether. Removal of the solvent afforded 430 mg of crude chloromethyl derivative. A portion (225 mg) was removed for further reactions. The remainder (205 mg) was flash chromatographed on silica gel and eluted with 40% ether/pentane to provide 137 mg of 2-chloromethyl-4-chlorosaccharin, mp 135°–136° C.

PREPARATION 3A

To a suspension of 6.0 g (0.03 mol) of cuprous iodide in 100 ml of THF was added 25 ml of dimethyl sulfide, and the resulting yellow solution was cooled to −78° C. and treated dropwise with a solution of 23 ml (0.06 mol) of a 3.0M solution of phenyl magnesium bromide in diethyl ether. The resulting pale yellow-orange solution was stirred at −78° C. under nitrogen for one hour and then treated with 3.02 g (0.03 mol) of 2-cyclohexenone in 10 ml of THF. The resulting mixture was allowed to warm to 0° C. over a two hour period, recooled to −78° C., treated with 15 ml of hexamethylphosphoramide, stirred for thirty minutes, treated with 8.0 g (0.09 mol) of methyl cyanoformate and allowed to warm to ambient temperature overnight. The reaction mixture was poured into 100 ml of 2N hydrochloric acid, and the organic phase was separated and the aqueous phase back-extracted with MDC. The combined organic extracts were taken to dryness in vacuo and the residue triturated with saturated ammonium chloride, then with water, then with brine and taken to dryness once again to give 3.2 g of methyl 2-phenylcyclohexan-6-one carboxylate as an oil.

The latter (3.0 g, 0.013 mol), 4.8 g (0.039 mol) of benzyl mercaptan and 1.0 g of Amberlyst ®-15 resin (Rohm and Haas) in chloroform was heated under reflux for twenty hours, the mixture treated with an additional 1.5 g of the resin and heated for an additional four hours. The mixture was then cooled to ambient temperature, filtered, the filtrate taken to dryness in vacuo, the residue triturated with hexane and the solid collected by filtration to give 0.85 g (19%) of a mixture of methyl 2-benzylthio-6-phenylcyclohex-2-ene carboxylate and methyl 2-benzylthio-6-phenylcyclohex-1-ene carboxylate, 0.6 g (0.0018 mol) of which was heated with 2.0 g of 2,3-dichloro-5,6-dicyanobenzoquinone in 25 ml of toluene with stirring under nitrogen for twenty-four hours. The mixture was filtered through a pad of silica gel, eluting with 2:1 MDC:hexane, and the eluate was taken to dryness to give 0.3 g (67%) of methyl 2-benzylthio-6-phenylbenzoate.

The latter (0.52 g, 0.0016 mol) dissolved in 10 ml of MDC was diluted with 20 ml of acetic acid and 5 ml of water, the mixture cooled to −10° C., and chlorine gas was bubbled through the mixture until the exothermic reaction subsided. The mixture was then stirred for ten minutes and taken to dryness in vacuo to give 0.41 g (85%) of methyl 2-chlorosulfonyl-6-phenylbenzoate which was dissolved in 10 ml of THF and added to 25 ml of a solution of concentrated ammonium hydroxide while cooling in an ice/acetone bath. The reaction mixture was extracted with MDC, the organic phase discarded, and the aqueous layer acidified to pH 1 with concentrated hydrochloric acid and extracted with MDC. The organic extracts, on washing with brine, drying and evaporation to dryness, afforded 0.33 g (97%) of 4-phenylsaccharin.

Following a procedure similar to that described in Preparation 1, the latter (0.33 g, 0.0012 mol) was reacted with 0.3 g (0.0019 mol) of chloromethyl phenyl sulfide in 15 ml of toluene in the presence of 0.08 g (0.0025 mol) of TBAB and the product, 2-phenylthiomethyl-6-phenylsaccharin (0.48 g, 100%), treated with sulfuryl chloride in MDC to give 0.36 g (95%) of 2-chloromethyl-4-phenylsaccharin.

PREPARATION 3B

To a suspension of anhydrous CuCN (2.16 g, 0.025 mol) in anhydrous ether (100 mL) at −78° C. was added tert butyllithium (29.0 mL of 1.7M solution in pentane, 0.05 mol). After being stirred at −78° C. for 1 hr and at −45° C. for 30 minutes, the reaction mixture was recooled to −78° C. A solution of cyclohexenone (2.4 g, 0.025 mol) in ether (25 mL) was added and stirring continued for 15 minutes at −78° C. and at −45° C. for 30 minutes. The resulting mixture was recooled to −78° C., and HMPA (10 mL) in ether (25 mL) was added. After 5 min, methyl cyanoformate (2.55 g, 0.03 mol) in ether (25 mL) was added and the reaction warmed to 0° C. over a 2 hr period. The resulting mixture was quenched with 2N HCl (100 mL), the layers were separated, and the organic phase was washed with saturated NH$_4$Cl solution (3×50 mL), water (2×50 mL), brine (1×50 mL) and dried (Na$_2$SO$_4$). Removal of the solvent in vacuo and purification by Kugelrohr distillation (bath temperature 100°–115° C. at 0.6 mm) afforded 4.7 g (88%) of methyl-2-(1,1-dimethylethyl)cyclohexan-6-one carboxylate.

The cyclohexanone (4.6 g, 0.022 mol) was mixed with benzylmercaptan (2.95 g, 0.024 mol) and the acidic clay montmorillonite, KSF (7.5 g) in anhydrous toluene (7.5 mL). The mixture was refluxed under nitrogen with azeotropic removal of water for 6 hr, cooled to room temperature and let stand overnight. The solids were filtered off and washed with ether. The combined filtrate was washed with 10% Na$_2$CO$_3$, water, brine and dried. Removal of the solvent in vacuo and purification of the residue by flash chromatography on silica gel (10% ether in hexanes) gave 4.4 g (66%) of a mixture of methyl 2-benzylthio-6-(1,1-dimethylethyl)cyclohex-2-ene carboxylate and 2-benzylthio-6-(1,1-dimethylethyl)cyclohex-1-ene carboxylate, which was stirred with DDQ (17.5 g, 0.077 mol) in toluene (50 mL) for 16 hr. The red reaction mixture was filtered through a 15 cm pad of silica gel, eluting with 6:3:1 hexanes:MDC:ether (1000 mL). The eluates were washed with 10% NaOH solution, water, brine and dried. Removal of the solvent in vacuo and purification by chromatography on silica gel (5% ether in hexanes) gave 1.6 g (40%) of methyl 2-benzylthio-6-(1,1-dimethyl)benzoate.

The benzylthiobenzoate (1.3 g, 0.004 mol) dissolved in MDC (5 mL) was diluted with acetic acid (25 mL) and water (2 mL), the mixture cooled to −10° C., and chlorine gas was bubbled until the exothermic reaction subsided. The mixture was then stirred for 10 minutes and taken to dryness in vacuo. Purification of the residue by flash chromatography on silica gel (1:1 hexanes:MDC) gave 0.8 g (67%) of methyl 2-chlorosulfonyl-6-(1,1-dimethylethyl)benzoate, which was dissolved in THF (5 mL) and added to a solution of concentrated ammonium hydroxide (25 mL) while cooling in an ice/acetone bath. After stirring at room temperature for 16 hr, the reaction mixture was concentrated in vacuo and acidified to pH 1 with 2N HCl. The separated solids were collected by filtration and crystallized from ether to give 0.64 g (95%) of 4-(1,1-dimethylethyl)saccharin, mp 185°–187° C.

The 4-(1,1-dimethylethyl)saccharin (0.025 g, 1.0 mmol) was mixed with chloromethyl phenyl sulifde (0.25 g, 1.5 mmol) and tetrabutyl ammonium bromide (0.2 g, 0.6 mmol) in toluene (25 mL) and refluxed under nitrogen for 16 hr. The resulting mixture was cooled to room temperature, evaporated to dryness and purified by chromatography on silica gel (80%) MDC in hexanes to give 0.35 g (98%) of 2-phenylthiomethyl-4-(1,1-dimethylethyl)saccharin, which was treated with sulfuryl chloride (0.25 g, 1.8 mmol) in MDC to give 0.21 g (75%) of 2-chloromethyl-4-(1,1-dimethylethyl)saccharin.

PREPARATION 4

A mixture of 3.22 g (0.012 mol) of 4-bromosaccharin [Japanese Pat. Disclosure 58/79,034, published May 12, 1983; C.A. 100, 7773w (1984)], 1.63 g (0.015 mol) of potassium t-butoxide, 0.39 g (0.0012 mol) of TBAB and 3.0 ml (0.022 mol) of chloromethyl phenyl sulfide in 100 ml of toluene was heated under reflux under a nitrogen atmosphere for eight hours and then stirred at ambient temperature for about sixteen hours. The reaction mixture was then diluted with ethyl acetate, and the organic layer was washed with dilute potassium carbonate, water and brine, dried over magnesium sulfate and taken to dryness in vacuo. The residual solid was recrystallized from toluene-hexane to give 3.86 g (84%) of 4-bromo-2-phenylthiomethylsaccharin, mp 174.5°–178° C.

To a solution of the latter (3.27 g, 0.0085 mol) in 85 ml of MDC was added, dropwise with stirring, 1.02 ml (0.0127 mol) of sulfuryl chloride. The mixture was stirred at ambient temperature for an hour and a half, concentrated in vacuo and the residue triturated with hexane and filtered to give 2.61 g of crude product which was recrystallized from toluene-hexane to give 2.24 g (85%) of 2-chloromethyl-4-bromosaccharin, mp 157°–159° C.

PREPARATION 5

To a solution of 8.0 ml (0.053 mol) of tetramethylethylenediamine (TMEDA) in 350 ml of THF at −70° C. was added 42 ml (0.055 mol) of a 1.3M solution of s-butyl lithium in cyclohexane and the mixture was stirred for fifteen minutes. To the solution was added dropwise with stirring a solution of 10.36 g (0.050 mol) of 2-methoxy-N,N-diethylbenzamide in 150 ml of THF while maintaining the temperature at −60° C. or below. After stirring for 20 minutes sulfur dioxide was bubbled into the reaction mixture, keeping the reaction temperature below −50° C., until the reaction mixture was acid to wet litmus paper. The mixture was stirred at ambient temperature for two hours, diluted with 450 ml of hexane, and the solid material which had separated was collected, dissolved in 200 ml of water and the mixture treated with 65 g of sodium acetate and 21.5 g (0.19 mol) of hydroxylamine-O-sulfonic acid in portions with stirring. The white solid which separated was collected and dried to give 7.04 g (49%) of 2-aminosulfonyl-6-methoxy-N,N-diethylbenzamide, mp 190°–194.5° C.

A mixture of the product (4.3 g, 0.015 mol) in 75 ml of dioxane and 25 ml of concentrated hydrochloric acid was heated on a steam bath for 70 hours, then cooled, concentrated in vacuo, diluted with water and ice and rendered strongly basic with concentrated sodium hydroxide. The mixture was washed with MDC, and the aqueous layer was acidified with dilute hydrochloric acid and extracted with MDC. The extracts were dried over magnesium sulfate and taken to dryness to give 1.29 g (40%) of 4-methoxysaccharin. In an alternative, and preferred, procedure, cyclization of 2-aminosulfonyl-6-methoxy-N,N-diethylbenzamide to 4-methoxysaccharin in 65% yield was carried out in refluxing glacial acetic acid for six and a half hours.

Following a procedure similar to that described in Preparation 4 above, 1.14 g (0.0053 mol) of the latter was reacted with 1.31 ml (0.0097 mol) of chloromethyl phenyl sulfide in toluene in the presence of 0.72 g (0.0064 mol) of potassium t-butoxide and 174 mg (0.00054 mol) of tetrabutylammonium bromide to give 1.23 g (69%) of 4-methoxy-2-phenylthiomethylsaccharin, mp 152.5°–154.5° C. (from ethyl acetate-hexane), 1.02 g (0.003 mol) of which was treated with 0.36 ml (0.0045 mol) of sulfuryl chloride in MDC to give 282 mg (36%) of 2-chloromethyl-4-methoxysaccharin, mp 169°–174° C.

PREPARATION 6A

To a solution of 4.74 ml (0.031 mol) of tetramethylethylenediamine in 300 ml of THF (passed through alumina prior to use) was added 5.8 g (0.03 mol) of 2-ethyl-N,N-diethylbenzamide. The solution was cooled to −78° C. and treated with a solution of 34.9 ml (0.031 mol) of a 0.9M solution of s-butyl lithium in cyclohexane. When addition was complete, the mixture was stirred for twenty minutes and then treated with a solution of 3.2 ml (0.04 mol) of ethyl iodide while maintaining the temperature at −78° C. The temperature was then allowed to rise to ambient temperature and the mixture stirred for about sixteen hours and then poured into water. The resulting oil was separated and chromatographed on silica gel, eluting with 10% ethyl acetate/hexane to give 2.86 g (43%) of 2-sec.-butyl-N,N-diethylbenzamide as a yellow oil.

Following a procedure similar to that described in Preparation 5 above, the latter (10.45 g, 0.045 mol), dissolved in 70 ml of THF, was added to a solution of 39.2 ml (0.047 mol) of a 1.2M solution of s-butyl lithium in cyclohexane and 7.1 ml (0.047 mol) of tetramethylethylenediamine in 250 ml of THF while maintaining the temperature at −78° C. When addition was complete the mixture was stirred for an additional one half hour at −78° C. and then treated with sulfur dioxide at −70° C. and then allowed to warm to room temperature. The mixture was taken to dryness in vacuo, and the residue was dissolved in water and added with stirring to a cold solution of 15.2 g (0.134 mol) of hydroxylamine-O-sulfonic acid and 15.4 ml (0.134 mol) of 35% sodium hydroxide to give 10.1 g (72%) of 2-aminosulfonyl-6-sec.-butyl-N,N-diethylbenzamide.

The latter (6.83 g, 0.22 mol) was dissolved in 100 ml of glacial acetic acid and the solution heated under reflux for thirteen hours and then taken to dryness. The residue was triturated with diethyl ether and collected by filtration to give 5.7 g (83%) of the diethylammonium salt of 4-sec.-butylsaccharin.

The latter (3.0 g, 0.0096 mol), on reaction with 1.13 ml (0.012 mol) of chloromethyl phenyl sulfide in toluene, afforded 3.47 g (100%) of 2-phenylthiomethyl-4-sec.-butylsaccharin.

Reaction of the latter (3.2 g, 0.0097 mol) with 2.3 ml (0.029 mol) of sulfuryl chloride in 20 ml of MDC afforded 2.4 g (87%) of 2-chloromethyl-4-sec.-butylsaccharin.

PREPARATION 6B

By a procedure analogous to that described for Preparation 6A, 9.2 g (32.9 mmol) of 3,4-dimethyoxy-2-propyl-N,N-diethylbenzamide was reacted with sulfur dioxide and 5.6 g (49.4 mmol) of hydroxylamine-O-sulfonic acid to provide 7.4 g (63%) of 2-aminosulfonyl-4,5-dimethoxy-6-propyl-N,N-diethylbenzamide which was cyclized in quantitative yield in acetic acid and phenylthiomethylated with 1.42 mL (15 mmol) of chloromethyl phenyl sulfide to provide 4.07 g of 5,6-dimethoxy-2-phenylthio-4-propylsaccharin. Reaction of 3.59 g (8.8 mmol) of the phenylthioether with 2.12 mL (26.4 mmol) sulfuryl chloride provided 2.84 g (97%) of 2-chloromethyl-5,6-dimethoxy-4-propylsaccharin.

The 3,4-dimethoxy-2-propyl-N,N-diethylbenzamide was obtained by the following procedure:

To a solution of 0.216 moles of n-butyllithium in 250 mL of ether at ambient temperature was added dropwise 138.2 g (0.216 mol) of veratrol in 100 mL of ether and 32.6 mL (0.216 mol) of TMEDA. The reaction was stirred at ambient temperature 14 hours and 21.9 mL (0.225 mol) of n-propyl iodide was added with cooling. The reaction was stirred 1 hour at RT and worked up with aqueous 1N HCl to give 14 g (36%) of 2,3-dimethoxybenzenepropane which was brominated with 14.52 g (81.6 mmol) of N-bromosuccinimide on 36 g of Kieselgel in 400 mL of CCl$_4$ according to the method of Hisatoshi et al. [Bull. Chem. Soc. Jap. 32, 591–593 (1989)] to give 19.6 g (98%) of 6-bromo-2,3-dimethoxybenzenepropane.

The bromobenzene (14.2 g, 54.8 mmol) was dissolved in 200 mL ether, cooled to $-78°$ C., and 25.2 mL (63 mmol) of 2.5 N n-butyllithium in hexane was added. The reaction was warmed to $0°$ C., held for an hour, and cooled to $-70°$ C., and 9 mL (71.2 mmol) of diethyl carbamyl chloride was added. The reaction was allowed to come to RT and was quenched with saturated ammonium chloride. After extraction and drying, the product was crystallized from hexane to provide 9.5 g (62%) of 3,4-dimethoxy-2-propyl-N,N-diethylbenzamide, mp 65°–67° C.

PREPARATION 6C

By a process analogous to that of Preparation 6B, 10.75 g (30 mmol) of 2-aminosulfonyl-4,5-dimethoxy-6-isopropyl-N,N-diethylbenzamide was cyclized to provide 6.43 g of 5,6-dimethoxy-4-isopropylsaccharin (mp 186°–188° C. from ether-hexane), 5 g (17.5 mmol) of which was phenylthiomethylated with 2.48 mL (26.3 mmol) of phenylthiomethylchloride according to the procedure of Preparation 5, and chlorinated with 3 equivalents of sulfuryl chloride to provide an 85% yield of 2-chloromethyl-5,6-dimethoxy-4-isopropylsaccharin, mp 117°–119° C. from ethyl acetate-hexane.

The requisite benzamide was obtained from 2,3-dimethoxy-α-methylbenzeneethane by bromination followed by carbamylation as in Preparation 6B, to provide the intermediate 3,4-dimethoxy-2-isopropyl-N,N-diethylbenzamide. A solution of 66 mL of 0.96M sec-butyllithium was added to 16.1 g (57.6 mmol) of the benzamide in 400 mL of THF at $-78°$ C. under nitrogen. After stirring 2 hours the orange anion was cannulated into excess sulfur dioxide at $-60°$ C. The reaction was allowed to come to room temperature and stirred for 18 hrs to remove SO$_2$. Ten milliliters of sulfuryl chloride was added at $0°$ C. and the reaction was stripped. The sulfonyl chloride was extracted into EtOAc-ether, washed with water, dried and stripped. The residue was dissolved in 80 mL of THF and 17 mL of conc. NH$_4$OH was added at $0°$ C. The reaction was stirred briefly at RT, stripped, and triturated in 2:1 etherhexane to provide 12.89 g (62%) of 2-aminosulfonyl-4,5-dimethoxy-6-isopropyl-N,N-diethylbenzamide, mp 138°–140° C.

PREPARATION 7

To a solution of 9.3 ml (0.058 mol) of tetramethylethylenediamine in 340 ml of THF at $-78°$ C. was added 52 ml of a 1.1M solution (0.057 mol) of s-butyl lithium in cyclohexane. The solution was then treated with a solution of 11.37 g (0.052 mol) of 2-propyl-N,N-diethylbenzamide in 75 ml of THF at $-78°$ C. and the solution stirred for fifteen minutes and then treated with a solution of 8.3 ml (0.104 mol) of ethyl iodide in THF. The solution was stirred for an hour and a half at $-78°$ C. and then quenched by the addition of saturated ammonium chloride added dropwise at $-78°$ C. The mixture was then allowed to warm to ambient temperature, diluted with diethyl ether, washed first with dilute hydrochloric acid, then with water, then with saturated sodium bicarbonate, then with brine, dried and taken to dryness to give 12.91 g of crude product which was chromatographed on silica gel, eluting with 10% ethyl acetate/hexane to give 3.23 g (25%) of 2-(3-pentyl)-N,N-diethylbenzamide as a yellow oil.

Following a procedure similar to that described in Preparation 5 above, the latter (3.05 g, 0.0115 mol) in THF was reacted with 10.5 ml (0.126 mol) of a 1.2M solution of s-butyllithium in cyclohexane in the presence of 2.1 ml (0.014 mol) of tetramethylenediamine. The resulting lithium salt was then reacted first with sulfur dioxide and then with sodium hydroxylamine-O-sulfonate to give 1.97 g (52%) of 2-aminosulfonyl-6-(3-pentyl)-N,N-diethylbenzamide as pale yellow crystals, mp 118°–120° C. (soft 102°), 1.84 g (0.0056 mol) of which was cyclized in 22 ml of refluxing glacial acetic acid to give 1.28 g (70%) of the diethylammonium salt of 4-(3-pentyl)-saccharin, mp 107.5°–109.5° C.

The latter (0.0037 mol), on reaction with 0.74 ml (0.0055 mol) of chloromethyl phenyl sulfide in the presence of 116 mg (0.0004 mol) of TBAB in 45 ml of toluene, afforded 1.93 g of 2-phenylthiomethyl-4-(3-pentyl)-saccharin as a pale yellow oil, 1.93 g (0.0037 mol) of which, on reaction with 0.59 ml (0.0073 mol) of sulfuryl chloride in 37 ml of MDC, afforded 1.2 g of 2-chloromethyl-4-(3-pentyl)saccharin as a pale yellow oil.

PREPARATION 8

A solution of 50.0 g (0.27 mol) of 2,4-dimethoxybenzoic acid in 60 ml (98.0 g, 0.82 mol) of thionyl chloride was heated under reflux for three hours, then cooled, and the excess thionyl chloride distilled off. The resulting 2,4-dimethoxybenzoyl chloride was dissolved in 150 ml of MDC and the solution treated with a solution of 68 ml (48 g, 0.66 mol) of diethylamine in 500 ml of MDC, cooled to $0°$ C. When addition was complete the mixture was stirred for fifteen hours at ambient temperature, then washed with saturated sodium bicarbonate, water and brine and taken to dryness and the residue distilled in vacuo to give 44.78 g (69%) of 2,4-dimethoxy-N,N-diethylbenzamide, bp 155°–163° C./0.4 mm.

Following a procedure similar to that described in Preparation 5 above, 10.0 g (0.042 mol) of the product in 250 ml of THF was reacted with 40.57 ml of a 1.1M solution (0.044 mol) of s-butyl lithium in cyclohexane and 6.35 ml (0.042 mol) of tetramethylethylenediamine in THF. The resulting lithium salt was then reacted first with about 40 ml of sulfur dioxide and then with an aqueous solution (0.13 mol) of sodium hydroxylamine- O-sulfonate to give 8.26 g of 2-aminosulfonyl-4,6-dimethoxy-N,N-diethylbenzamide, 7.0 g of which (0.022 mol) was cyclized in 80 ml of refluxing glacial acetic acid to give 6.6 g (94%) of the diethylammonium salt of 4,6-dimethoxysaccharin which was used as such in the next step without further purification.

The latter (6.0 g, 0.019 mol), on reaction with 3.82 ml (0.028 mol) of chloromethyl phenyl sulfide in the presence of 0.611 g (0.0019 mol) of TBAB in 200 ml of toluene, afforded 6.2 g (89%) of 2-phenylthiomethyl-4,6-dimethoxysaccharin, 5.82 g of which (0.016 mol), on reaction with 3.23 g (0.0019 mol) of sulfuryl chloride in 100 ml of MDC, afforded 4.63 g (100%) of 2-chloromethyl-4,6-dimethoxysaccharin, mp 185°–187° C.

PREPARATION 9A–9G

Following a procedure similar to that described above in Preparation 5, substituting for the 2-methoxy-N,N-diethylbenzamide used therein an appropriate 2-$R_1$-$R_2$-$R_3$-substituted-N,N-diethylbenzamide, the following 4-$R_1$-$R_2$-$R_3$-2-halomethylsaccharins, where, in each instance, $R_3$ is hydrogen, listed in TABLE A were prepared via the corresponding 2-phenylthiomethylsaccharins. Wherever available, the melting point (°C.), recrystallization solvent and yield are given for each of the 2-unsubstituted saccharins, the 2-phenylthiomethylsaccharins and the 2-chloromethylsaccharins in columns headed "mp/Solv." and "Yield". In all instances, the intermediate 2-phenylthiomethylsaccharins were used directly in the subsequent step without further characterization or purification.

TABLE A

| Prep. | $R_1$/$R_2$ | Sacc. mp/Solv. | Yield | 2-$C_6H_5SCH_2$-Sacc. mp/Solv. | Yield | 2-$ClCH_2$-Sacc. mp/Solv. | Yield |
|---|---|---|---|---|---|---|---|
| 9A | H<br>7-Cl | 260–262 | 93 | — | 100 | 158.0–160.0<br>i-PrOH | 51 |
| 9B | CH(CH$_3$)$_2$<br>H | 177.0–178.0<br>MeOH | 88 | — | 100 | 93.0–96.0<br>i-PrOH-Cyc.hex | 100 |
| 9C | CH$_3$O<br>5-CH$_3$O | (a) | 64 | — | 100 | 190.0–192.0 | 76 |
| 9D | COOCH$_3$<br>H | (b)<br>EtOAc-hex. | 76 | — | 65 | 186.0–187.0 | |
| 9E | C$_2$H$_5$O<br>H | (a) | 96 | — | 95 | 139.0–140.0 | 97 |
| 9F | (CH$_3$)$_2$CHO<br>H | | 87 | — | 75 | 142.5–143.5 | 94 |
| 9G | C$_2$H$_5$<br>5,7-(CH$_3$O)$_2$ | i-PrOH | 67 | — | 52 | — | 99 |

(a) Isolated and used in the next step as the diethylammonium salt.
(b) The 2-unsubstituted-saccharin was prepared by cyclization of dimethyl 3-aminosulfonylphthalate in methanol in the presence of a molar equivalent of sodium methoxide. The phthalate ester was prepared by diazotization of dimethyl 3-aminophthalate, decomposition of the diazonium salt with sulfur dioxide in the presence of cupric chloride and reaction of the resulting dimethyl 2-chlorosulfonylphthalate with ammonia. (84% yield overall).

PREPARATION 10

Following a procedure similar to that described in Preparation 2, reaction of 18.3 g (0.1 mol) of saccharin with 70 ml of 37% formalin in ethanol afforded 3.58 g (70%) of 2-hydroxymethylsaccharin. The latter (25 g, 0.117 mol) was reacted with 63.3 g (0.234 mol) of phosphorus tribromide in diethyl ether to give 29.8 g (92%) of 2-bromomethylsaccharin, mp 155°–157° C.

PREPARATION 11

To a solution of 4 g (0.0175 mol) of 6-nitrosaccharin in 240 ml of ethanol was added 4.4 g (0.0175 mol) of thallium ethoxide, and the mixture was allowed to stand at room temperature for one hour, cooled for about 16 hours and the precipitated solid collected and dried to give 7.6 g (100%) of the thallium salt of 6-nitrosaccharin. The product was suspended in 50 ml of DMF and the mixture treated with 3.07 g (0.0194 mol) of chloromethyl phenyl sulfide, the mixture warmed at about 63° C. for five hours, allowed to stand at ambient temperature for about 16 hours, and then poured into ice water. The crude product, obtained by filtration, was stirred in MDC and filtered to remove thallium salts. The filtrate was freed of solvent, and the resultant pale yellow solid was sonicated with warm ethanol and once again collected and dried to give 4.6 g (75%) of 6-nitro-2-phenylthiomethylsaccharin, mp 161°–163° C. The latter, on reaction with sulfuryl chloride in MDC using the procedure described above in Preparation 4, afforded 3.7 g of 2-chloromethyl-6-nitrosaccharin.

PREPARATION 12

A solution of 49.8 g (0.199 mol) of 2-hydroxy-5-(1,1,3,3-tetramethylbutyl)benzoic acid in 200 ml of methanol was heated to 50° C. and then treated dropwise with about 80 g of sulfuric acid at a rate to maintain the reaction under reflux. The reaction mixture was heated under reflux for an additional 11 hours, then cooled and partitioned between water and ethyl acetate. The organic layer was washed with saturated sodium bicarbonate, then with brine, dried over sodium sulfate and taken to dryness to give 48.6 g (92%) of methyl 2-hydroxy-5-(1,1,3,3-tetramethylbutyl)benzoate.

The latter dissolved in 250 ml of DMF was treated first with 40.4 g (0.36 mol) of 1,4-diazabicyclo[2.2.2]octane followed by 33.4 g (0.27 mol) of N,N-dimethylchlorothiocarbamate and 100 ml of DMF. The reaction mixture was heated at 45° C. for about eight hours, cooled, poured into ice/water and concentrated hydrochloric acid and then extracted with ethyl acetate. The combined organic extracts were washed with dilute hydrochloric acid, then with sodium bicarbonate and then with brine, dried and taken to dryness to give 48.2 g (76%) of methyl 2-(N,N-dimethylthiocarbamyloxy-5-(1,1,3,3-tetramethylbutyl)benzoate which was heated at 220° C. for 15 hours, then cooled, dissolved in toluene and chromatographed on silica, eluting with 1:9 ethyl acetate:toluene, to give 3.6 g (14%) of methyl 2-(N,N- dimethylcarbamylthio)-5-(1,1,3,3-tetramethylbutyl)benzoate.

A solution of the latter (0.025 mol) in 40 ml of MDC was treated, with stirring, with 80 ml of glacial acetic acid, followed by 16 ml of water. The reaction mixture was cooled to 0° C., and chlorine was bubbled through the reaction mixture for about five minutes while maintaining the temperature between 5° and 24° C. The reaction was stirred for an additional 30 minutes, concentrated in vacuo, and the remaining solution poured into ice water. Extraction of the mixture with ethyl acetate and isolation of the product from the combined organic extracts afforded 6.8 g (78%) of methyl 2-chlorosulfonyl-5-(1,1,3,3-tetramethylbutyl)benzoate.

The product (9.0 g, 0.026 mol) was dissolved in THF and added to 100 ml of concentrated ammonium hydroxide with cooling in an ice bath. The resulting solution was stirred for about 16 hours, then concentrated in vacuo and the concentrated solution acidified to pH 3 with concentrated hydrochloric acid. The mixture was stirred for several hours, and the separated solid collected, washed with water and dried to give 9.0 g of 5-(1,1,3,3-tetramethylbutyl)saccharin, mp 213°–215° C.

Following a procedure similar to that described in Preparation 11, 9.0 g (0.30 mol) of the product was reacted with thallium ethoxide in ethanol and the resulting thallium salt reacted with 3.33 g (0.021 mol) of chloromethyl phenyl sulfide in DMF to give 5.76 g (66%) of 2-phenylthiomethyl-5-(1,1,3,3-tetramethylbutyl)saccharin, 3.3 g (0.007 mol) of which was treated with 0.944 g of sulfuryl chloride in MDC to give 1 g (41%) of 2-chloromethyl-5-(1,1,3,3-tetramethyl)butyl saccharin.

PREPARATION 13

Following a procedure similar to that described in Preparation 12 above, 15.5 g (0.086 mol) of ethyl 2-hydroxy-6-methylbenzoate was reacted with 15.9 g (0.129 mol) of N,N-dimethylchlorothiocarbamate in the presence of 19.3 g (0.172 mol) of 1,4-diazabicyclo[2.2.2]octane in DMF to give 22.1 g (96%) of ethyl 2-(N,N-dimethylthiocarbamyloxy)-6-methylbenzoate which was heated at 220° C. for about 10 hours. The product was purified by chromatography on silica gel in MDC to give ethyl 2-(N,N-dimethylcarbamylthio)-6-methylbenzoate as a red-brown oil.

A solution of the latter (22.6 g, 0.0844 mol) in 170 ml of MDC was treated with 340 ml of glacial acetic acid and 68 ml of water while cooling in an ice/acetone bath, and chlorine was bubbled through the reaction mixture for 10–15 minutes. The reaction vessel was evacuated to remove excess chlorine and MDC and the mixture poured into water and partitioned between MDC and water. The organic layer, on drying and evaporation to dryness, afforded 19 g of ethyl 2-chlorosulfonyl-6-methylbenzoate, 5 g (0.019 mol) of which was reacted with concentrated ammonium hydroxide in THF to give 6.1 g (67%) of 4-methylsaccharin.

Following a procedure similar to that described in Preparation 11 above, the product (10.1 g, 0.0512 mol) was converted to the thallium salt by reaction with 12.8 g (0.0512 mol) of thallium ethoxide in ethanol and the thallium salt reacted with 6.7 g (0.0427 mol) of chloromethyl phenyl sulfide in DMF to give 6.85 g (50%) of 2-phenylthiomethyl-4-methylsaccharin.

Reaction of the latter (6.7 g, 0.021 mol) with sulfuryl chloride in MDC afforded 4.9 g (95%) of 2-chloromethyl-4-methylsaccharin.

PREPARATION 14A

A mixture of 75 g (0.36 mol) of 3,3-dithiobispropionic acid, 102 ml of thionyl chloride and a catalytic amount of pyridine was stirred for about 24 hours and then evaporated to dryness in vacuo. The residue was treated with MDC and evaporated to dryness again to remove residual thionyl chloride and pyridine to give 87 g (98%) of the corresponding bis acid chloride, 44.8 g (0.18 mol) of which was dissolved in THF and added dropwise to a solution of 77.16 g (0.72 mol) of benzylamine in THF. The mixture was stirred for two hours at 40°–45° C., cooled and the precipitated solid collected, washed with water and dried to give 59 g (84%) of 3,3-dithiobispropionic acid N,N'-dibenzylcarboxamide, mp 162°–165° C.

Reaction of 7.0 g (0.018 mol) of the latter with 10.25 g (0.076 mol) of sulfuryl chloride in MDC gave a mixture of 2-benzyl-2H-isothiazol-3-one and 5-chloro-2-benzyl-2H-isothiazol-3-one which were largely separated from one another by sonication in MDC (which solubilized most of the former). The insoluble material was collected by filtration and chromatographed on silica gel with MDC. There was thus obtained 5-chloro-2-benzyl-2H-isothiazol-3-one, mp 58°–68° C.

A solution of 10 g (0.044 mol) of the latter in MDC was cooled to 0° C. and the solution treated with 7.6 g (0.044 mol) of 3-chloroperbenzoic acid, the mixture stirred for 10 minutes and then treated with a second 7.6 g portion of the perbenzoic acid. The reaction mixture was filtered, the filter washed with MDC and the filtrate washed with saturated sodium bicarbonate, then with brine, dried over sodium sulfate and taken to dryness and the residue chromatographed in MDC on silica gel, the product being eluted with 50:50 hexane: MDC, to give 7.15 g (46%) of 5-chloro-2-benzyl-2H-isothiazol-3-one 1-oxide.

A solution of 1.1 g (0.0045 mol) of the latter in 8 ml of benzene was treated with 0.55 g (0.0051 mol) of 2-methoxyfuran and the solution heated in a pressure bottle at 70° C. for 1½ hours and then cooled and the solid collected, washed with benzene and dried to give 2-benzyl-7-hydroxy-4-methoxybenzisothiazol-3-one 1-oxide, mp 235°–237° C.

A mixture of the product (1.85 g, 0.006 mol), 2.48 g (0.018 mol) of potassium carbonate and 1.70 g (0.012 mol) of methyl iodide in acetone was heated under reflux for 1½ hours and then cooled and poured into water. The solid which separated was collected by filtration, washed with water and dried to give 1.70 g (89%) of 2-benzyl-4,7-dimethoxybenzisothiazol-3-one 1-oxide, 1.13 g (0.0035 mol) of which was oxidized with 1.20 g (0.007 mol) of 3-chloroperbenzoic acid in MDC using the procedure described above to give 1.03 g (88%) of 2-benzyl-4,7-dimethoxysaccharin.

A mixture of 2.07 g (0.0062 mol) of the product, 1.37 g (0.02 mol) of ammonium formate and 1.5 g of 10% palladium-on-charcoal catalyst in 80 ml of methanol was heated under reflux for one hour, then cooled and filtered, and the filtrate taken to dryness to give 0.92 g (57%) of the ammonium salt of 4,7-dimethoxysaccharin.

A solution of 1.11 g (0.0042 mol) of the ammonium salt was dissolved in DMF, 0.67 g (0.0042 mol) of chloromethyl phenyl sulfide was added, and the solution heated under reflux for eight hours and then cooled and poured into ice water. The solid which separated was collected, washed with water and dried to give 0.50 g (33%) of 2-phenylthiomethyl-4,7-dimethoxysaccharin.

Reaction of the latter (0.5 g, 0.0013 mol) with sulfuryl chloride in MDC using the procedure described above in Preparation 4 afforded 0.22 g (58%) of 2-chloromethyl-4,7-dimethoxysaccharin.

PREPARATIONS 14B and 14C

Following a procedure similar to that described in Preparation 14A, other 2-chloromethylsaccharin derivatives were prepared as follows:

PREPARATION 14B

Reaction of 5.8 g (0.02 mol) of 5-chloro-2-benzyl-2H-isothiazol-3-one-1-oxide with 3.76 g (0.0335 mol) of 2-ethoxyfuran afforded 3.05 g (40%) of 2-benzyl-4-ethoxy-7-hydroxybenzisothiazol-3-one 1-oxide, 5.7 g of which was reacted with 3.6 g (0.0197 mol) of 2-(2-methoxyethoxy)ethyl bromide in the presence of 4.95 g (0.0358 mol) of potassium carbonate in 125 ml of methyl ethyl ketone and 25 ml of DMF to give 7.0 g (93%) of 2-benzyl-4-ethoxy-7-[2-(2-methoxyethoxy)ethoxy]benzisothiazol-3-one 1-oxide, which was oxidized as before with 3-chloroperbenzoic acid in MDC to give 2-benzyl-4-ethoxy-7-[2-(2-methoxyethoxy)ethoxy]saccharin. Debenzylation of 6.6 g (0.015 mol) of the latter with 3.34 g (0.053 mol) of ammonium formate in the presence of 6.4 g of 10% palladium-on-charcoal catalyst in methanol afforded the ammonium salt of 4-ethoxy-7-[2-(2-methoxyethoxy)ethoxy]-saccharin, which was reacted with 2.38 g (0.015 mol) of chloromethyl phenyl sulfide in 100 ml of DMF to give 1.46 g (21%) of 2-phenylthiomethyl-4-ethoxy-7-[2-(2-methoxyethoxy)-ethoxy]saccharin, mp 73°-75° C. (from isopropanol). Treatment of 1.4 g (0.0029 mol) of the product with 0.4 g (0.0029 mol) of sulfuryl chloride in MDC afforded 1.16 g (100%) of 2-chloromethyl-4-ethoxy-7-[2-(2-methoxyethoxy)ethoxy]saccharin.

PREPARATION 14C

Reaction of 3.03 g (0.01 mol) of 2-benzyl-7-hydroxy-4-methoxybenzisothiazol-3-one-1-oxide (Preparation 14A) with 2.01 g (0.011 mol) of 2-(2-methoxyethoxy)ethyl bromide in methyl ethyl ketone in the presence of 2 g (0.015 mol) of potassium carbonate afforded 2.58 g (64%) of 2-benzyl-4-methoxy-7-[2-(2-methoxyethoxy)ethoxy]benzisothiazol-3-one-1-oxide, which, on oxidation with 1.1 g (0.0063 mol) of 3-chloroperbenzoic acid in MDC, gave 2-benzyl-4-methoxy-7-[2-(2-methoxyethoxy)ethoxy]saccharin. Debenzylation of 0.25 g (0.0006 mol) of the product with 0.13 g (0.0021 mol) of ammonium formate in methanol in the presence of 0.25 g of 10% palladium-on-charcoal gave 0.21 g (100%) of the ammonium salt of 4-methoxy-7-[2-(2-methoxyethoxy)ethoxy]-saccharin. Reaction of 1.4 g (0.004 mol) of the ammonium salt with 0.63 g (0.004 mol) of chloromethyl phenyl sulfide in DMF afforded 2-phenylthiomethyl-4-methoxy-7-[2-(2-methoxyethoxy)ethoxy]saccharin, which, on reaction with sulfuryl chloride in MDC, afforded 0.53 g (35%) of 2-chloromethyl-4-methoxy-7-[2-(2-methoxyethoxy)ethoxy]saccharin.

PREPARATION 15

A solution of 1.89 g (0.011 mol) of diethylamino sulfur trifluoride (DAST) in 20 ml of MDC was added to a suspension of 2.13 g (0.01 mol) of 2-hydroxymethylsaccharin in 25 ml of MDC while maintaining the reaction mixture at −78° C.

The reaction mixture was stirred at −78° C. for one hour, the temperature allowed to slowly rise to ambient temperature, the mixture stirred for 16 hours and then poured into ice-water. The organic layer was separated and washed with water, dried over magnesium sulfate and taken to dryness to give 2.2 g of product which was recrystallized from ethyl acetate to give 1.6 g (74%) of 2-fluoromethylsaccharin, mp 96°-98° C.

PREPARATION 16A

To a solution of 0.5 g (0.0025 mol) of 4-methylsaccharin in THF cooled to −78° C. by a dry ice/acetone bath was added, dropwise with stirring, a solution of 5.2 ml of a 1.3M solution of s-butyl lithium in cyclohexane. The mixture was stirred an additional hour at −78° C. and then treated with 0.16 ml (0.025 mol) of methyl iodide over a 1½ hour period. The mixture was stirred for an hour and 45 minutes, quenched in 25 ml of 1N hydrochloric acid, the reaction mixture rendered basic, the aqueous mixture extracted with chloroform and then acidified and extracted with ethyl acetate. The combined organic extracts were washed with 10% sodium thiosulfate, then with brine, dried over sodium sulfate and taken to dryness to give a product, whose PMR spectrum indicated a mixture consisting of 74% of 4-ethylsaccharin and 21% of 4,7-dimethylsaccharin.

Following a procedure similar to that described in Preparation 4 above, the crude material (0.47 g, 0.0022 mol) was reacted with 0.24 ml (0.0028 mol) of chloromethyl phenyl sulfide in toluene in the presence of tetrabutylammonium bromide, and the product chromatographed on silica gel, eluting with MDC, 5 ml fractions being collected. The first 420 ml of eluate were discarded. The next 20 fractions, on evaporation, afforded 0.07 g of material, predominantly 2-phenylthiomethyl-4,7-dimethylsaccharin, which was set aside. The next 25 fractions afforded 0.37 g of 2-phenylthiomethyl-4-ethylsaccharin, which was reacted with sulfuryl chloride in MDC to give 0.19 g (66%) of 2-chloromethyl-4-ethylsaccharin.

PREPARATION 16B

Following a procedure similar to that described in Preparation 16A, 10 g (0.051 mol) of 4-methylsaccharin in THF was reacted with 86 ml (0.10 mol) of a 1.18M solution of s-butyl lithium in cyclohexane and the resulting solution treated with 4.5 ml (0.050 mol) of ethyl iodide to give 10.15 g (89%) of 4-propylsaccharin, which, on reaction with 5.32 ml (0.056 mol) of chloromethyl phenyl sulfide in toluene in the presence of tetrabutylammonium bromide, afforded a crude mixture from which was isolated by flash chromatography on silica gel 2-phenylthiomethyl-4-propylsaccharin as an oil, 1.8 g (0.0052 mol) of which, on reaction with 1.25 ml (0.016 mol) of sulfuryl chloride in MDC, afforded 0.94 g (66%) of 2-chloromethyl-4-propylsaccharin.

PREPARATION 16C

A preferred alternative to Preparation 16A is as follows:

To a solution of 5.13 g (25 mmol) of N,N,2-triethylbenzamide in THF (50 mL) at −78° C. was added a solution of LDA (Aldrich 2.0M, 15.63 mL, 31.25 mmol). The solution was warmed to −10° C. with ice water over 1 hr, then cooled to −78° C. with dry ice-acetone. TMSCl (6.34 mL, 50 mmol) was added neat at −78° C. and then reaction brought to room temperature after 1 hr. The reaction was quenched with saturated NH$_4$Cl and extracted with ether (2×100 mL), dried over MgSO$_4$, stripped and the residue distilled in a Kugelrohr (130°–140° C., 0.65 mm) to obtain 6.51 g (94%) of N,N-diethyl-2-[1-(trimethylsilyl)ethyl]benzamide.

To a solution of sec BuLi (0.97M, 5.10 mL, 4.96 mmol), TMEDA (0.75 mL, 4.96 mmol) in THF at −78° C. was added the amide (1.25 g, 4.50 mmol) in THF. Excess $SO_2$ in THF was added quickly at −78° C. then warmed to room temperature. The THF was removed in vacuo then reacted at 0° C. with two equivalents of a 1:1 solution of sodium hydroxide (0.36 g, 9.0 mmol) and hydroxylamine-O-sulfonic acid (1.0 g, 9.0 mmol) in $H_2O$. The reaction was stirred at room temperature for 4 hrs, extracted with EtOAc and flash chromatographed on silica gel with 20% ethyl acetate/hexane to give 0.62 g (47%) of 2-aminosulfonyl-N,N-diethyl-6-[1-(trimethylsilyl)ethyl]benzamide. The benzamide (0.95 g, 2.66 mol) was refluxed in glacial acetic acid (20 mL) for 18 hr, stripped to dryness, triturated with hot cyclohexane (30 mL) and a trace of EtOAc (3 mL), cooled with scratching and filtered. There was obtained 0.81 g (85%) of 4-[1-(trimethylsilyl)ethyl]saccharin, mp 123°–125° C.

to the trimethylsilylethylsaccharin (0.25 g, 0.70 mmol) in DMF (9 mL) at room temperature was added $H_2O$ (1 mL) and cesium fluoride (0.75 g, 4.94 mmol, 7 equivalents). After 7 hr the reaction was poured into 5% NaOH and extracted with EtOAc. The aqueous layer was acidified with 12N HCl and extracted with $Et_2O$-EtOAc (1:1), dried over $Na_2SO_4$, filtered and stripped to give a colorless solid in quantitative yield. It was recrystallized from 5% $Et_2O$-hexanes to give 0.091 g (64%) of 4-ethylsaccharin, mp 183°–185° C.

PREPARATION 17

The 0.07 g sample of material obtained in the early fractions from the chromatographic separation described above in Preparation 16A consisting predominantly of 2-phenylthiomethyl-4,7-dimethylsaccharin was reacted with 0.05 ml of sulfuryl chloride in MDC and the product recrystallized from cyclohexane-ethyl acetate to give 20 mg (51%) of 2chloromethyl-4,7-dimethylsaccharin, mp 107°–108° C.

PREPARATION 18A

To a solution of 40.0 g (0.174 mol) of 2-isopropyl-4-methoxybromobenzene in 600 ml of diethyl ether at 0° C. was added 103.68 ml (0.175 mol) of a 1.69M solution of butyl lithium in diethyl ether. When the addition was complete the solution was cooled to 0° C. for one hour and stirred for an additional five hours at ambient temperature, then recooled to −78° C. and treated with a solution of 23.68 g (0.175 mol) of N,N-diethylcarbamyl chloride in 80 ml of diethyl ether. The resulting solution was stirred for about 12 hours while the reaction temperature was allowed to rise and then quenched with saturated ammonium chloride solution. The aqueous and organic layers were separated, the aqueous layer backextracted with ethyl acetate and the combined organic extracts washed once with brine, then dried and the solution taken to dryness to give a crude product which was flashed chromatographed on silica gel, eluting with 30% ethyl acetate/hexane to give 34.4 g (79%) of 2-isopropyl-4-methoxy-N,N-diethylbenzamide as an oil which was used as such in the next step without further purification. The oil can be distilled, if desired, and boils at 123°–129° C./0.2–0.3 mm.

Following a procedure similar to that described in Preparation 5 above, the latter (15.0 g, 0.060 mol) in 100 ml of diethyl ether was reacted with 77.8 ml (0.784 mol) of a 1.2M solution of s-butyl lithium in cyclohexane in the presence of 6.98 g (0.06 mol) of tetramethylethylenediamine. The resulting lithium salt was then reacted first with 50 ml of sulfur dioxide and then with 0.181 mol of sodium hydroxylamine-O-sulfonate to give 11.6 g (59%) of 2-aminosulfonyl-6-isopropyl-4-methoxy-N,N-diethylbenzamide, mp 103°–105° C. (from ethyl acetate/hexane), 11.0 g (0.034 mol) of which was cyclized in 200 ml of refluxing glacial acetic acid to give 10.3 g of the diethylammonium salt of 4-isopropyl-6-methoxysaccharin, mp 132°–135° C.

The latter (0.030 mol), on reaction with 6.14 ml (7.25 g, 0.046 mol) of chloromethyl phenyl sulfide in the presence of 0.98 g (0.003 mol) of TBAB in 250 ml of toluene, afforded 10.1 g (88%) of 2-phenylthiomethyl-4-isopropyl-6-methoxysaccharin as an oil, 9.7 g (0.026 mol) of which, on reaction with 3.1 ml (5.21 g, 0.039 mol) of sulfuryl chloride in MDC, afforded 6.9 g (88%) of 2-chloromethyl-4-isopropyl-6-methoxysaccharin, mp 151°–152° C.

PREPARATION 18B

An alternative procedure was also followed:

To a soution of 300 mL of N,N,N',N'-tetramethylethylenediamine (TMEDA) (1.99 moles) in 4 L of anhydrous ether was added 1550 mL of sec-BuLi (1.3M) and the system was cooled to −70° C. under a nitrogen atmosphere. A solution of 454.2 g of 2-isopropyl-4-methoxy N,N-diethylbenzamide (1.82 moles) in 300 mL of anhydrous ether was added dropwise over 30 minutes (the temperature was maintained at or below −60° C. during the addition). After the addition was complete, the reaction was stirred at −70° C. for one hour and allowed to warm to −50° C. After holding the temperature at −50° C. for 30 minutes, the mixture was cooled back to −70° C. To this stirred solution was added via cannulating tube a solution of 200 g of $SO_2$ in 200 mL of dry ether precooled to −40° C. under positive nitrogen pressure over a 20-minute period. The temperature of the reaction mixture during the addition was maintained below −40° C. (A white powdery precipitate of aryllithium sulphinate separated out almost immediately). After the addition, the ice-bath was removed and the reaction was allowed to stir at ambient temperature for two hours. It was cooled to −5° C. and to this stirred solution was added 190 mL of sulfuryl chloride (2.36 moles) dropwise over a 15-minute period maintaining the temperature below 10° C. during the addition. After further stirring for 30 minutes at 0°–5° C., a white insoluble precipitate was filtered off and washed with 2 L of anhydrous ether. Removal of the solvent at atmospheric pressure afforded the sulfonyl chloride as a crude dark oil. This crude sulfonyl chloride was dissolved in 1.4 L of THF, cooled to −10° C., and 540 mL of concentrated $NH_4OH$ (28%) was added in portions over 15 minutes (the temperature was kept at 15° C. or below throughout the addition). After stirring for 15 minutes at ambient temperature, the THF and excess ammonia were removed under vacuum to give a dark oil, which was diluted with 6.0 L of water and acidified with 3N HCl to pH 1. The light yellow solid was collected by filtration and washed with 800 mL of water. The solid was dried at 60° C. under vacuum for 18 hours and recrystallized from a mixture of 800 mL of ethyl acetate and 3 L of hexane to give 429 g (72%) of 2-aminosulfonyl-6-isopropyl-4-methoxy-N,N-diethylbenzamide, mp 122°–125° C.

A solution of 429.6 g of the diethylbenzamide (1.31 mole) in 1.5 L of acetic acid was refluxed for 20 hours. It was cooled to room temperature and the solvent removed under vacuum. The oily residue was dissolved in 6 L of water and adjusted to pH 1 with 6N HCl. The crude product was collected by filtration and washed with 2 L of water. The solid was dried at 60° C. under vacuum for 18 hours and recrystallized from ethyl acetate/hexane to give 303 g (91%) 4-isopropyl-6-methoxysaccharin, mp 188° C.

To a suspension of 24 g of paraformaldehyde (0.8 mole) and 86.4 g of chlorotrimethylsilane (1.6 moles) in 200 mL of 1,2-dichloroethane was added 0.8 ml anhydrous tin(IV) chloride and the resulting solution stirred on a steam bath for one hour. At the end of this period, 51 g of 4-isopropyl-6-methoxysaccharin (0.2 mole) was added to the clear solution and the reaction mixture was further refluxed for 18 hours. It was cooled to room temperature, poured into water, the organic layer separated and washed with 50 mL of 2N sodium hydroxide solution. The organic layer was dried over anhydrous magnesium sulfate and concentrated under vacuum to give crude product. It was purified by crystallization from ethyl acetate/hexane to give 57 g (87%) of 2-chloromethyl-4-isopropyl-6-methoxysaccharin, mp 151° C.

PREPARATION 19

To a solution of 1.0 g (0.0039 mol) of 4-isopropyl-6-methoxysaccharin in 15 ml of MDC was added at ambient temperature 1.28 g (5.12 ml) of a 1M solution of boron tribromide in MDC. When addition was complete the reaction mixture was heated under reflux for about five hours, cooled, taken to dryness in vacuo and the residue treated with ice and saturated sodium bicarbonate. The aqueous solution was extracted once with ethyl acetate and then acidified to pH 1 with concentrated hydrochloric acid. Extraction of the mixture with ethyl acetate/diethyl ether (8:2), drying the organic extracts and removal of the solvent in vacuo afforded 0.9 g (96%) of 6-hydroxy-4-isopropylsaccharin as a white crystalline solid which was used as such in the next step.

An alternative procedure was also used. To a stirred suspension of 62.74 g (0.47 mol) of AlCl$_3$ in 500 mL of chloroform at 0° C. was added 43.9 g (0.7 mol) of ethanethiol. Within minutes a clear solution formed. To this a solution of 20.0 g (0.078 mol) of 4-isopropyl-6-methoxysaccharin in 550 mL of chloroform was added over a 30-min period. This solution was allowed to warm to RT and stirred for 3-4 hr at 60° C. After cooling, the mixture was poured into ice-water and acidified with dilute HCl. The solid which separated was collected by filtration, washed with water and dried to give 18.4 g (97%) of 6-hydroxy-4-isopropylsaccharin.

Following a procedure similar to that described in Preparation 4 above, the latter (0.004 mol) was reacted with 0.61 ml (0.0046 mol) of chloromethyl phenyl sulfide in toluene in the presence of 0.133 g (0.004 mol) of TBAB to give 0.32 g (21%) of 6-hydroxy-4-isopropyl-2-phenylthiomethylsaccharin, mp 127°-129.5° C., 1.78 g of which was treated with 0.43 ml (0.73 g) of sulfuryl chloride in MDC to give 1.2 g (84%) of 2-chloromethyl-6-hydroxy-4-isopropylsaccharin, mp 149°-150° C.

PREPARATION 19A

Following procedures similar to those described in Preparation 19, 4-methoxysaccharin can be converted successively to 4-hydroxysaccharin, 4-hydroxy-2-phenylthiomethylsaccharin and 2-chloromethyl-4-hydroxysaccharin.

PREPARATION 20

Five grams (0.0207 mol) of 6-hydroxy-4-isopropylsaccharin was dissolved in 150 ml of methanol and 3.4 g (0.0104 mol) of Cs$_2$CO$_3$ was added. The mixture was stirred for 3-4 hr at RT. The excess methanol was removed under reduced pressure and the residue was dried for 2 hr under high vacuum. The residue was then dissolved in 110 mL of DMF and 0.32 g (0.0209 mol) of chloromethyl phenyl sulfide was added. The stirred mixture was heated at 70°-75° C. for 12 hr, cooled, treated with ice water and extracted with 600 mL of 4:1 ethyl acetate:ether. The organic layer was washed with water and saturated NaCl and dried. The solvent was removed under reduced pressure. The residue was purified by flash chromatography with 20% ethyl acetate in MDC. There was obtained 4.5 g (60%) of 6-hydroxy-4-isopropyl-2-phenylthiomethylsaccharin, mp 150°-151.5° C. which, on reaction with sulfuryl chloride as described in Preparation 19, yielded 2-chloromethyl-6-hydroxy-4-isopropylsaccharin as before.

PREPARATION 21

To a solution of 5-chloro-2-benzyl-4-isothiazolin-3-one (J. Het. Chem. 8, 571, 1971) (9.4 g, 0.04 mol) in MDC (100 mL) was added in one portion 80-85% 3-chloroperoxybenzoic acid (10.8 g, 0.06 mol) and the resulting mixture stirred at room temperature overnight under nitrogen. The precipitated solids were filtered off and washed with MDC (50 mL). The combined filtrate was evaporated to near dryness and the residue partitioned between ethyl acetate (300 mL) and saturated NaHCO$_3$ (100 mL). The layers were separated and the organic phase washed with saturated NaHCO$_3$ (2×100 mL), brine (1×100 mL) and dried. Removal of the solvent in vacuo afforded 10.0 g (99%) of 5-chloro-2-benzyl-4-isothiazolin-3(2H)-one 1-oxide as a pale yellow oil.

The 1-oxide (10.0 g, 0.04 mol) in glacial acetic acid (200 mL) was treated with 30% H$_2$O$_2$ (100 mL, 0.88 mol) and heated on a steam bath for 2 hr during which time an additional 30 mL (0.26 mol) of 30% H$_2$O$_2$ was added. After heating on a steam bath for an additional hour, the reaction mixture was cooled to room temperature and poured into ice cold water (1L) and stirred. The precipitated solids were collected by filtration, washed with water (2×100 mL), hexanes and air dried to give 4.8 g (45%) of 5-chloro-2-benzyl-4-isothiazolin-3(2H)-one 1,1-dioxide as a colorless solid.

The dioxide (1.2 g, 4.7 mmol) was mixed with 2.02 g (11 mmol) of 2-trimethylsiloxy-5-methyl-hexa-1,3-diene (prepared from 5-methyl-hex-3-ene according to the method of E. J. Corey et al., Tet. Lett. 495, 1984) in toluene (50 mL) and refluxed for a period of 20 hr under nitrogen. The resulting mixture was cooled to room temperature and concentrated in vacuo. The residue was dissolved in THF (25 mL) and treated with 2N HCl (10 mL). After stirring under nitrogen at room temperature for 10 min, ether (100 mL) was added and the layers separated. The organic phase was washed with water, brine, dried and evaporated to dryness to give a pale yellow foam. The foam was dissolved in toluene (30 mL), DBN (1.5 mL) was added and stirred at room temperature for 2 hr. MDC (100 ml) and 2N HCl (50 mL) were added and stirring continued for 5 min. The layers were separated and the organic phase washed with water, brine and dried. Removal of the solvent in vacuo and purification of the residue by flash chromatography on silica gel (5:4:1, hexanes:MDC:ether) gave 0.6 g (39%) of 2-benzyl-4-isopropyl-6-oxo-tetrahydrosaccharin as a pale yellow foam.

The tetrahydrosaccharin (0.59 g, 1.7 mmol) was dissolved in toluene (50 mL), dimethylamine hydrochloride (1.5 g, 18.0 mmol) and 4 A sieves (2.0 g) were added. The resulting mixture was refluxed with azeotropic removal of water for 96 hr. It was necessary to add additional dimethylamine hydrochloride (0.8 g, 10.0 mmol) and 4 A sieves every 12 hr during this 96 hr period at the end of which time, the reaction mixture was cooled to room temperature and filtered. The filter cake was washed with diethyl ether (100 mL) and the combined filtrates were concentrated in vacuo to give 0.63 g (99%) of 2-benzyl-4-isopropyl-6-dimethylamino-(4,5)-dihydrosaccharin as a pale yellow solid.

To a solution of the dihydrosaccharin (0.63 g, 1.7 mmol) in refluxing chloroform (50 mL) was added activated manganese dioxide (4.3 g, 49.5 mmol) in portions over a period of 4 hr. After the addition of the last portion of manganese dioxide, the reaction was refluxed for an additional hr, cooled to room temperature and filtered through a pad of Super-Cel, eluting with ethyl acetate. The combined eluates were concentrated in vacuo and the residue purified by flash chromatography on silica gel (5:4:1, hexanes:MDC:ether) to give 0.32 g (50%) of 2-benzyl-4-isopropyl-6-dimethylaminosaccharin as a colorless solid.

The 2-benzylsaccharin (0.32 g, 0.9 mmol) in methanol (20 mL) was treated with ammonium formate (0.24 g, 3.8 mmol) and 10% Pd on Carbon (0.25 g) and refluxed for 1 hr, cooled to room temperature and filtered through a pad of Super-Cel, eluting with methanol (100 ml). The combined eluates were concentrated in vacuo. The residue was dissolved in MDC (10 mL), glacial acetic acid (0.25 mL) was added, stirred for 5 min and evaporated to dryness in vacuo to give 0.25 g (100%) of 4-isopropyl-6-dimethylaminosaccharin as a colorless foam.

Following a procedure similar to that described in Preparation 1, a mixture of 4-isopropyl-6-dimethylaminosaccharin (0.27 g, 1.0 mmol), chloromethyl phenylsulfide (0.32 g, 2.0 mmol) and tetrabutylammonium bromide (0.1 g, 0.2 mmol) in toluene was converted to 0.22 g (56%) of 2-phenylthiomethyl-4-isopropyl-6-dimethylaminosaccharin which was treated with sulfuryl chloride (1.86 mL of 0.31 M solution, 0.6 mmol) to give 0.15 g of a yellow gum that contained 25% (by NMR) of 2-chloromethyl-4-isopropyl-6-dimethylamino-7-chlorosaccharin.

PREPARATION 22

Thirty-one grams of 4-isopropyl-1,2-dimethoxybenzene was treated with N-bromosuccinimide followed by butyllithium and diethyl carbamyl chloride as in Preparation 6B to yield 15.2 g of 2-isopropyl-4,5-dimethoxy-N,N-diethylbenzamide as a viscous oil. The benzamide was treated according to Preparation 18B with butyllithium and sulfur dioxide followed by sulfuryl chloride then ammonia to provide 4.5 g of the sulfonamide, mp 181°-182° C. from ether. This was cyclized in acetic acid as in Preparation 18B to obtain 2.86 g of 6,7-dimethoxy-4-isopropylsaccharin, mp 210°-212° C. from ethyl acetate-hexane.

To a solution of 0.5 g of 4-isopropyl-6,7-dimethoxysaccharin in 3 mL of DMF was added 0.5 mL of diisopropylethylamine at room temperature. After 15 min, 0.35 g chloromethyl phenyl sulfide was added and the mixture heated at 80° C. for 16 hr. The reaction mixture was poured into EtOAc and washed with aqueous $Na_2CO_3$ solution, aqueous 2N HCl solution, saturated aqueous NaCl solution. The organic layer was dried over $Na_2SO_4$ and the solvents removed. Chromatography with MDC gave 0.35 g of desired product, which was used immediately. Treatment of the 0.35 g sample of phenylthiomethylsaccharin in 3 mL of MDC with 0.1 mL of sulfuryl chloride for 30 min at 20° C. followed by removal of solvents and trituration with hexane gave 0.3 g of 2-chloromethyl-6,7-dimethoxy-4-isopropylsaccharin.

PREPARATION 23

To a solution of 5.7 g of methyl piperonylate in 20 mL of dry ether was added 30 mL of 3.0 methyl magnesium bromide in ether at 0° C. over 20 min. The mixture was stirred for 20 hr then diluted with 200 mL of ether and washed with water. The organic layer was dried with $Na_2SO_4$ and the solvents removed to yield 5.6 g of crude 3,4-dimethoxy-(1'-hydroxy-1'-methylethyl)benzene. This material was immediately treated in 50 mL of acetic acid with 1 g of 10% Pd/C under 50 psi of hydrogen for 20 hr. Filtration to remove catalyst and removal of solvent yielded 4.5 g of 5-isopropyl-1,3-benzodioxole. The isopropyldioxole was brominated, amidated, sulfonated and cyclized as in Preparation 22 to yield 700 mg of 4-isopropyl-6,7-methylenedioxysaccharin, mp 226°-228° C. from ethyl acetate/hexane. Five hundred milligrams of the saccharin was chloromethylated as in Preparation 22 to provide 300 mg of 2-chloromethyl-4-isopropyl-6,7-methylenedioxysaccharin, mp 174°-176° C.

PREPARATION 24

Following the procedure of Preparation 18A, 5 g of 2-bromo-N,N-dimethylaniline was converted to 3.5 g of N,N-diethyl-2-dimethylaminobenzamide. The amide was reacted by the method of Preparation 18B to provide 65 mg of 4-dimethylaminosaccharin, mp 228°-229° C. from ether-hexane.

Reaction of 4-dimethylaminosaccharin with chloromethyl phenyl sulfide in the presence of potassium t-butoxide and tetrabutylammonium bromide affords 4-dimethylamino-2-phenylthiomethylsaccharin. Reaction of the latter with sulfuryl chloride in MDC affords 4-dimethylamino-2-chloromethylsaccharin. Alternatively, reaction of 4-dimethylaminosaccharin with paraformaldehyde and chlorotrimethylsilane in the presence of a catalytic amount of stannic chloride in ethylene dichloride affords 4-dimethylamino-2-chloromethylsaccharin.

PREPARATION 25

To a solution of 1.0 g (2.75 mm) of 6-hydroxy-4-isopropyl-2-phenylthiomethylsaccharin in THF was added 0.73 g (2.78 mm) of triphenylphosphine, 0.14 g (3.04 mm) of ethanol and 0.48 g (2.76 mm) of diethyl azodicarboxylate at RT. The mixture was stirred for 10-12 hr. The reaction was repeated starting with 3.73 g (10.28 mm) of the 6-hydroxy compound. The reaction mixtures were combined and then flash chromatographed on silica gel with ethyl acetate in hexane (10% followed by 15%) to give 4.37 g (85%) of 6-ethoxy-4- isopropyl-2-phenylthiomethylsaccharin, mp 111.5°–112.5° C., which was converted to 2-chloromethyl06-ethoxy-4-isopropylsaccharin in 91% yield, mp 127°–128° C., following the procedure of Preparation 18A.

Other 4-$R_1$-$R_2$-$R_3$-saccharins of formula IV useful as intermediates for the preparation of compounds of formula I can be prepared as follows.

Reaction of 2-trifluoromethylbenzoic acid with thionyl chloride affords 2-trifluoromethylbenzoyl chloride, which, on reaction with diethylamine, affords 2-trifluoromethyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 2-trifluoromethyl-6-aminosulfonyl-N,N-diethylbenzamide, which, on heating in glacial acetic acid, affords 4-trifluoromethylsaccharin.

Similarly, reaction of 2-trichloromethylbenzoic acid with thionyl chloride affords 2-trichloromethylbenzoyl chloride, which, on reaction with diethylamine, affords 2-trichloromethyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 2-trichloromethyl-6-aminosulfonyl-N,N-diethylbenzamide, which, on heating in glacial acetic acid, affords 4-trichloromethylsaccharin.

Reaction of 4-cyclohexylbenzoic acid with thionyl chloride affords 4-cyclohexylbenzoyl chloride, which, on reaction with diethylamine, affords 4-cyclohexyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 4-cyclohexyl-2-aminosulfonyl-N,N-diethylbenzamide, which, on heating in glacial acetic acid, affords 6-cyclohexylsaccharin.

Benzylation of 6-nitrosaccharin affords 2-benzyl-6-nitrosaccharin which on reduction with stannous chloride and aqueous hydrogen chloride affords 2-benzyl-6-aminosaccharin. Reaction of the latter with methanesulfonyl chloride, trifluoromethylsulfonyl chloride or trichloromethylsulfonyl chloride in MDC in the presence of pyridine followed by transfer hydrogenolysis of the 2-benzyl protecting group affords, respectively, 6-methylsulfonylaminosaccharin, 6-trifluoromethylsulfonylaminosaccharin or 6-trichloromethylsulfonylaminosaccharin.

Diazotization of 6-aminosaccharin with nitrous acid in an acid medium and decomposition of the resulting diazonium salt in the presence of cupric cyanide or cupric chloride and sulfur dioxide, or cupric chloride and an alkali metal salt of methyl mercaptan or trifluoromethyl mercaptan affords, respectively, 6-cyanosaccharin, 6-chlorosulfonylsaccharin, 6-methylthiosaccharin or 6-trifluoromethylthiosaccharin. Reaction of the 6-chlorosulfonylsaccharin in situ with ammonia or methanesulfonylamide affords, respectively, 6-aminosulfonylsaccharin and 6-methanesulfonylaminosulfonylsaccharin. Oxidation of 6-methylthiosaccharin and 6-trifluoromethylthiosaccharin with two molar equivalents of 3-chloroperbenzoic acid affords 6-methylsulfonylsaccharin and 6-trifluoromethylsulfonylsaccharin, respectively.

Hydrolysis of 6-cyanosaccharin by heating with aqueous sodium hydroxide affords saccharin-6-carboxylic acid. N-Benzylation of 6-cyanosaccharin affords 2-benzyl-6-cyanosaccharin. The latter on alkaline hydrolysis affords 2-benzylsaccharin-6-carboxylic acid which on conversion to 2-benzylsaccharin-6-carboxylic acid chloride by reaction with thionyl chloride followed by exhaustive hydrogenation over palladium-carbon affords 6-hydroxymethylsaccharin. Oxidation of the latter with pyridine:chromium trioxide (2:1) complex (Collins reagent) in MDC affords 6-formylsaccharin, which on reductive amination with ammonia affords 6-aminomethylsaccharin.

Reaction of 4-trifluoromethylbenzoic acid with thionyl chloride affords 4-trifluoromethylbenzoyl chloride, which on reaction with diethylamine, affords 4-trifluoromethyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 4-trifluoromethyl-2-aminosulfonyl-N,N-diethylbenzamide, which on heating in glacial acetic acid, affords 6-trifluoromethylsaccharin.

Reaction of 4-trichloromethylbenzoic acid with thionyl chloride affords 4-trichloromethylbenzoyl chloride, which, on reaction with diethylamine, affords 4-trichloromethyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 4-trichloromethyl-2-aminosulfonyl-N,N-diethylbenzamide, which, on heating in glacial acetic acid, affords 6-trichloromethylsaccharin.

Reaction of 2-ethenylbenzoic acid with thionyl chloride affords 2-ethenylbenzoyl chloride, which on reaction with diethylamine, affords 2-ethenyl-N,N-diethylbenzamide. Reaction of the latter with s-butyl lithium and reaction of the resulting lithium salt with sulfur dioxide followed by sodium hydroxylamine-O-sulfonate affords 2-ethenyl-6-aminosulfonyl-N,N-diethylbenzamide, which, on heating in glacial acetic acid, affords 4-ethenylsaccharin.

Reaction of 2-ethenyl-6-aminosulfonyl-N,N-diethylbenzamide with bromine affords 2-(1,2-dibromoethyl)-6-aminosulfonyl-N,N-diethylbenzamide which, on reaction with sodium amide in ammonia affords 2-ethynyl-6-aminosulfonyl-N,N-diethylbenzamide, which, on heating in glacial acetic acid, affords 4-ethynylsaccharin.

Reaction of ethyl 2-aminobenzoate with two molar equivalents of benzyl chloride in acetone in the presence of potassium carbonate affords ethyl 2-(N,N-dibenzylamino)benzoate which, on saponification in aqueous ethanolic potassium hydroxide and isolation of the product from a neutral medium, affords 2-(N,N-dibenzylamino)benzoic acid.

Reaction of the latter with thionyl chloride affords 2-(N,N-dibenzylamino)benzoyl chloride, which, on reaction with diethylamine, affords 2-(N,N-dibenzylamino)-N,N-diethylbenzamide. Reaction of the latter with s-butyl lithium and reaction of the resulting lithium salt with sulfur dioxide followed by sodium hydroxylamine-O-sulfonate affords 2-(N,N-dibenzyl)-6-aminosulfonyl-N,N-diethylbenzamide, which, on heating in glacial acetic acid, affords 4-(N,N-dibenzylamino)saccharin which, on catalytic debenzylation with hydrogen over palladium-on-charcoal, affords 4-aminosaccharin. Reductive alkylation of the latter with one molar equivalent of formaldehyde in formic acid affords 4-methylaminosaccharin.

Selective N-benzylation of the cesium salt of 6-hydroxy-4-isopropylsaccharin (Preparation 19) with benzyl bromide and reaction of the 2-benzyl-6-hydroxy-4-isopropylsaccharin with N,N-diethylthiocarbamyl chloride in DMF using the procedure described above in Preparation 12 affords 2-benzyl-4-isopropyl-6-(N,N-diethylthiocarbamyloxy)saccharin which, on heating, rearranges to 2-benzyl-4-isopropyl-6-(N,N-diethylcarbamylthio)saccharin. The latter, on hydrolysis with alkali, affords 2-benzyl-4-isopropyl-6-mercaptosaccharin which on reaction with methyl iodide, and transfer hydrogenolysis affords 4-isopropyl-6-methylthiosaccharin. Oxidation of the latter with one or two molar equivalents of 3-chloroperbenzoic acid affords 4-isopropyl-6-methylsulfinylsaccharin and 4-isopropyl-6-methylsulfonylsaccharin.

Reaction of 2-isopropyl-4-fluorobenzoic acid with thionyl chloride affords 2-isopropyl-4-fluorobenzoyl chloride, which, on reaction with diethylamine, affords 2-isopropyl-4-fluoro-N,N-diethylbenzamide. Reaction of the latter with s-butyl lithium and reaction of the resulting lithium salt with sulfur dioxide followed by sodium hydroxylamine-O-sulfonate affords 2-isopropyl-4-fluoro-2-aminosulfonyl-N,N-diethylbenzamide, which, on heating in glacial acetic acid, affords 4-isopropyl-6-fluorosaccharin.

Reaction of the latter with thiophenol, 4-methylphenylthiophenol, 4-methoxyphenylthiophenol, 4-chlorophenylthiophenol, 1-mercapto-4-methylnaphthalene or 1-mercaptonaphthalene by heating the reactants in DMF affords, respectively, 4-isopropyl-6-phenylthiosaccharin, 4-isopropyl-6-(4-methylphenylthio)saccharin, 4-isopropyl-6-(4-methoxyphenylthio)saccharin, 4-isopropyl-6-(4-chlorophenylthio)saccharin, 4-isopropyl-6-(4-methyl-1-naphthylthio)saccharin and 4-isopropyl-6-(1-naphthylthio)saccharin, oxidation of which in each case with one or two molar equivalents of 3-chloroperbenzoic acid affords 4-isopropyl-6-phenylsulfinylsaccharin, 4-isopropyl-6-phenylsulfonylsaccharin, 4-isopropyl-6-(4-methylphenylsulfinyl)saccharin, 4-isopropyl-6-(4-methylphenylsulfonyl)saccharin, 4-isopropyl-6-(4-methoxyphenylsulfinyl)saccharin, 4-isopropyl-6-(4-methoxyphenylsulfonyl)saccharin, 4-isopropyl-6-(4-chlorophenylsulfinyl)saccharin, 4-isopropyl-6-(4-chlorophenylsulfonyl)saccharin, 4-isopropyl-6-(4-methyl-1-naphthylsulfinyl)saccharin, 4-isopropyl-6-(4-methyl-1-naphthylsulfonyl)saccharin, 4-isopropyl-6-(1-naphthylsulfinyl)saccharin and 4-isopropyl-6-(1-naphthylsulfonyl)saccharin.

Reaction of 2-benzyl-6-hydroxy-4-isopropylsaccharin with one molar equivalent of acetic anhydride, benzoyl chloride or 1-naphthylcarboxylic acid chloride followed in each case by transfer hydrogenolysis affords, respectively, 4-isopropyl-6-acetoxysaccharin, 4-isopropyl-6-benzoyloxysaccharin and 4-isopropyl-6-(1-naphthylcarbonyloxy)saccharin.

Heating 4-isopropyl-6-fluorosaccharin in DMF with azetidine, pyrrolidine, piperidine, morpholine, 1-benzylpiperazine, 1-methylpiperazine, imidazole, t-butyl alpha-aminoacetate or ammonia affords, respectively, 4-isopropyl-6-(1-azetidinyl)saccharin, 4-isopropyl-6-(1-pyrrolidinyl)saccharin, 4-isopropyl-6-(1-piperidinyl)saccharin, 4-isopropyl-6-(4-morpholinyl)saccharin, 4-isopropyl-6-(4-benzyl-1-piperazinyl)saccharin, 4-isopropyl-6-(4-methyl-1-piperazinyl)saccharin, 4-isopropyl-6-(1-1H-imidazolyl)saccharin, 4-isopropyl-6-(carbo-t-butoxymethylamino)saccharin and 4-isopropyl-6-aminosaccharin.

Catalytic debenzylation of 4-isopropyl-6-(4-benzyl-1-piperazinyl)saccharin with hydrogen over palladium-on-charcoal affords 4-isopropyl-6-(1-piperazinyl)saccharin.

Hydrolysis of 4-isopropyl-6-(carbo-t-butoxycarbonylmethylamino)saccharin with dilute hydrochloric acid and isolation of the product from a neutral medium affords 4-isopropyl-6-carboxymethylaminosaccharin.

Reaction of 4-isopropyl-6-aminosaccharin with one molar equivalent of acetyl chloride affords 4-isopropyl-6-acetylaminosaccharin.

Saponification of 4-carbomethoxysaccharin (Preparation 9D) to the corresponding saccharin-4-carboxylic acid by alkaline hydrolysis, conversion of the acid to the corresponding acid chloride by reaction of the acid with thionyl chloride and reaction of the acid chloride with ammonia affords saccharin-4-carboxamide.

Diazotization of aminosaccharin with nitrous acid in an acid medium and decomposition of the resulting diazonium salt in the presence of cupric cyanide affords 4-cyanosaccharin.

The $4\text{-}R_1\text{-}R_2\text{-}R_3\text{-}2$-chloromethylsaccharins of formula VI listed in TABLE B where, in each instance, $R_3$ is hydrogen and X is Cl, can be prepared by reaction of the $4\text{-}R_1\text{-}R_2\text{-}R_3$-saccharins so-prepared with chloromethyl phenyl sulfide in the presence of potassium t-butoxide and tetrabutylammonium bromide, followed by reaction of the resulting $4\text{-}R_1\text{-}R_2\text{-}R_3\text{-}2$-phenylthiomethylsaccharins with sulfuryl chloride in MDC; and/or by reaction of the $4\text{-}R_1\text{-}R_2\text{-}R_3$-saccharins so prepared with paraformaldehyde and chlorotrimethylsilane in the presence of a catalytic amount of stannic chloride in ethylene dichloride.

TABLE B

| Preparation | $R_1$ | $R_2$ |
|---|---|---|
| 26 | $CF_3$ | H |
| 27 | $CCl_3$ | H |
| 28 | H | 6-cyclohexyl |
| 29 | H | $6\text{-}CH_3SO_2NH$ |
| 30 | H | $6\text{-}CF_3SO_2NH$ |
| 31 | H | $6\text{-}CCl_3SO_2NH$ |
| 32 | H | 6-CN |
| 33 | H | $6\text{-}CONH_2$ |
| 34 | H | $6\text{-}NH_2SO_2$ |
| 35 | H | $6\text{-}CH_3SO_2NHSO_2$ |
| 36 | H | $6\text{-}CH_3SO_2$ |
| 37 | H | $6\text{-}CF_3SO_2$ |
| 38 | H | 6-HOOC |
| 39 | H | $6\text{-}HOCH_2$ |
| 40 | H | 6-OHC |
| 41 | H | $6\text{-}NH_2CH_2$ |
| 42 | H | $6\text{-}CF_3$ |
| 43 | H | $6\text{-}CCl_3$ |
| 44 | $CH=CH_2$ | H |
| 45 | $C\equiv CH$ | H |
| 46 | $NH_2$ | H |
| 47 | $CH_3NH$ | H |
| 48 | $CH(CH_3)_2$ | $6\text{-}CH_3S$ |
| 49 | $CH(CH_3)_2$ | $6\text{-}CH_3SO$ |
| 50 | $CH(CH_3)_2$ | $6\text{-}CH_3SO_2$ |
| 51 | $CH(CH_3)_2$ | 6-F |
| 52 | $CH(CH_3)_2$ | $6\text{-}C_6H_5S$ |
| 53 | $CH(CH_3)_2$ | $6\text{-}(4\text{-}CH_3C_6H_4S)$ |
| 54 | $CH(CH_3)_2$ | $6\text{-}(4\text{-}CH_3OC_6H_4S)$ |
| 55 | $CH(CH_3)_2$ | $6\text{-}(4\text{-}ClC_6H_4S)$ |
| 56 | $CH(CH_3)_2$ | $6\text{-}(4\text{-}CH_3\text{-}1\text{-naphthyl-S})$ |
| 57 | $CH(CH_3)_2$ | 6-(1-naphthyl-S) |
| 58 | $CH(CH_3)_2$ | $6\text{-}C_6H_5SO$ |
| 59 | $CH(CH_3)_2$ | $6\text{-}C_6H_5SO_2$ |
| 60 | $CH(CH_3)_2$ | $6\text{-}(4\text{-}CH_3C_6H_4SO)$ |
| 61 | $CH(CH_3)_2$ | $6\text{-}(4\text{-}CH_3C_6H_4SO_2)$ |

TABLE B-continued

| Preparation | R$_1$ | R$_2$ |
|---|---|---|
| 62 | CH(CH$_3$)$_2$ | 6-(4-CH$_3$OC$_6$H$_4$SO) |
| 63 | CH(CH$_3$)$_2$ | 6-(4-CH$_3$OC$_6$H$_4$SO$_2$) |
| 64 | CH(CH$_3$)$_2$ | 6-(4-ClC$_6$H$_4$SO) |
| 65 | CH(CH$_3$)$_2$ | 6-(4-ClC$_6$H$_4$SO$_2$) |
| 66 | CH(CH$_3$)$_2$ | 6-(4-CH$_3$-1-naphthyl-SO) |
| 67 | CH(CH$_3$)$_2$ | 6-(4-CH$_3$-1-naphthyl-SO$_2$) |
| 68 | CH(CH$_3$)$_2$ | 6-(1-naphthyl-SO) |
| 69 | CH(CH$_3$)$_2$ | 6-(1-naphthyl-SO$_2$) |
| 70 | CH(CH$_3$)$_2$ | 6-CH$_3$COO |
| 71 | CH(CH$_3$)$_2$ | 6-C$_6$H$_5$COO |
| 72 | CH(CH$_3$)$_2$ | 6-(1-naphthyl-COO) |
| 73 | CH(CH$_3$)$_2$ | 6-(1-azetidinyl) |
| 74 | CH(CH$_3$)$_2$ | 6-(1-pyrrolidinyl) |
| 75 | CH(CH$_3$)$_2$ | 6-(1-piperidinyl) |
| 76 | CH(CH$_3$)$_2$ | 6-(4-morpholinyl) |
| 77 | CH(CH$_3$)$_2$ | 6-(4-benzyl-1-piperazinyl) |
| 78 | CH(CH$_3$)$_2$ | 6-(4-methyl-1-piperazinyl) |
| 79 | CH(CH$_3$)$_2$ | 6-(1-1H-imidazolyl) |
| 80 | CH(CH$_3$)$_2$ | 6-(NHCH$_2$COOC$_4$H$_9$-t) |
| 81 | CH(CH$_3$)$_2$ | 6-NH$_2$ |
| 82 | CH(CH$_3$)$_2$ | 6-(1-piperazinyl) |
| 83 | CH(CH$_3$)$_2$ | 6-(NHCH$_2$COOH) |
| 84 | CH(CH$_3$)$_2$ | 6-(CH$_3$CONH) |
| 85 | CONH$_2$ | H |
| 86 | CH | H |

PREPARATION 87

Reaction of isothiazole-5-carboxaldehyde with lithium 3-(triphenylphosphoranylidene)propanoate under standard Wittig conditions provides 4-(5-isothiazolyl)-3-butenoic acid which is reduced and cyclized with aluminum chloride to provide 4-oxo-4,5,6,7-tetrahydro-1,2-benzisothiazole. The 4-oxo compound is reacted with methylenetriphenyl phosphorane under standard Wittig conditions and a methylene is inserted into the resulting 4-methylene compound via a Simmons Smith reaction to provide 6,7-dihydrospiro[1,2-benzisothiazole-4(5H),1'-cyclopropane] which is oxidized with hydrogen peroxide in acetic acid to give 6,7-dihydrospiro[3-oxo-1,2-benzisothiazole-4(5H),1'-cyclopropane 1,1-dioxide] (4-spirocyclopropyl-4,5,6,7-tetrahydrosaccharin). The latter is chloromethylated according to the procedure of Preparation 1 to give 2-chloromethyl-4-spirocyclopropyl-4,5,6,7-tetrahydrosaccharin.

PREPARATION 88

2-Benzyl-4-isopropyl-6-oxotetrahydrosaccharin of Preparation 21 is reduced with sodium borohydride and methylated with methyl iodide in the presence of sodium hydride to afford 2-benzyl-4-isopropyl-6-methoxytetrahydrosaccharin. This is debenzylated and chloromethylated as in Preparation 21 to provide 2-chloromethyl-4-isopropyl-6-methoxy-4,5,6,7-tetrahydrosaccharin.

PREPARATION 89

To freshly distilled cyclopentadiene (25 mL) at 0° C. was added 4-bromo-2-(tert-butyl)isothiazol-3(2H)-one 1,1-dioxide (*Helv. Chim. Acta*, 72, 1416, 1989) (7.9 g, 0.03 mol). After stirring at 0° C. under nitrogen for 16 hr, the reaction mixture was concentrated in vacuo. The residue was purified by filtering through silica gel, eluting with hexanes (500 mL) followed by 20% ethyl acetate in hexanes (500 mL) followed by 20% ethyl acetate in hexanes (500 mL). The eluates were concentrated in vacuo to give 9.8 g (100%) of the norbornene adduct, 3a-bromo-2-t-butyl-3a, 4,7,7a-tetrahydro-4,7-methano-1,2-benzisothiazol-3(2H)-one 1,1-dioxide, as a white solid.

The adduct (0.4 g, 1.2 mmol) in 25 mL of ethyl acetate containing 5% Pd on CaCO$_3$ (0.2 g) was stirred under one atmosphere of hydrogen for 4 hr, and the reaction mixture was filtered through a pad of silica gel, eluting with ethyl acetate (100 mL). The eluates were concentrated in vacuo and the residue crystallized from hexanes to give 0.4 g (100%) of the bromo norbornane, 3a-bromo-2-t-butyl-3a,4,5,6,7,7a-hexahydro-4,7-methano-1,2-benzisothiazol-3(2H)-one 1,1-dioxide, as a white crystalline solid.

To a solution of the bromo norbornane (3.7 g, 0.011 mol) in toluene (25 mL) at 0°C. was added diazabicyclononene (1.37 g, 0.011 mol) in toluene (10 mL). After stirring at 0° C. for 20 min, silica gel (25 g) was added to the reaction mixture. The resulting slurry was loaded on top of a 15 cm pad of silica gel and eluted with 20% ethyl acetate in hexanes (800 mL). The eluates were concentrated in vacuo to give 2.8 g (100%) of the dehydrobrominated compound, 2-t-butyl-4,5,6,7-tetrahydro-4,7-methano-1,2-benzisothiazol-3(2H)-one 1,1-dioxide, as a white solid.

The dehydrobrominated compound (2.8 g, 0.011 mol) in trifluoroacetic acid (30 mL) was heated at reflux for 48 hr and let stand at room temperature for 4 days. The resulting mixture was concentrated in vacuo, treated with methanol (20 mL) and evaporated to dryness. The residue was taken up in ether (100 mL) and washed with saturated NaHCO$_3$ (1×50 mL). The layers were separated and the aqueous phase acidified to pH 1 with 2N HCl and extracted with MDC (2×100 mL). The combined organic extracts were dried and concentrated in vacuo to give 0.9 g (42%) of the bicyclo(2.2.1)saccharin derivate, 4,5,6,7-tetrahydro-4,7-methano-1,2-benzisothiazol-3(2H)-one 1,1-dioxide (4,5,6,7-tetrahydro-4,7-methanosaccharin), as a white solid.

A mixture of the bicyclo(2.2.1)saccharin derivative (0.9 g, 5 mmol), chloromethyl phenylsulfide (0.07 g, 7 mmol) and tetrabutylammonium bromide (0.36 g, 0.16 mmol) in toluene (50 mL) was refluxed under nitrogen for 16 hr, cooled to room temperature and evaporated to dryness under vacuum. The residue was purified by flash chromatography on silica gel (100 g) using 100% MDC as the eluant to give 1.05 g (72%) of the corresponding 2-phenylthiomethyl derivative as a viscous oil.

The latter (1.05 g, 3 mmol) in dichloromethane (100 mL) was treated with sulfuryl chloride (0.66 g, 5 mmol) and stirred for 2 hr. The resulting yellow solution was diluted with MDC (100 mL), washed with saturated NaHCO$_3$ solution, dried and concentrated in vacuo. The residue was purified by flash chromatography on silica gel (33% MDC in hexanes) to give 0.66 g (81%) of 2-chloromethyl-4,5,6,7-tetrahydro-4,7-methano-1,2-benzisothiazol-3(2H)-one 1,1-dioxide (2-chloromethyl-4,5,6,7-tetrahydro-4,7-methanosaccharin).

PREPARATIONS 90 AND 91

By process analogous to those of Preparation 89, it is contemplated that cyclohexadiene or 1,1-dimethylcyclopentadiene can be reacted with 4-bromo-2-(tert-butyl)isothiazol-3 (2H)-one 1,1-dioxide to give, respectively, 3a-bromo-2-t-butyl-3a,4,7,7a-tetrahydro-4,7-ethano(or 4,7-dimethylmethano)-1,2-benzisothiazol-3(2H)-one 1,1-dioxide which can be hydrogenated to give 3a-bromo-2-t-butyl-3a,4,5,6,7,7a-hexahydro-4,7-ethano(or 4,7-dimethylmethano)-1,2-benzisothiazol- 3(2H)-one 1,1-dioxide which can be dehydrobrominated to give 2-t-butyl-4,5,6,7-tetrahydro-4,7-ethano(or 4,7-dimethylmethano)-1,2-benzisothiazol-3(2H)-one 1,1-dioxide which can be dealkylated to give 4,5,6,7-tetrahydro-4,7-ethano(or 4,7-dimethylmethano)-1,2-benzisothiazol-3(2H)-one 1,1-dioxide which can be reacted with chloromethyl phenylsulfide to give 2-phenylthiomethyl-4,5,6,7-tetrahydro-4,7-ethano(or 4,7-dimethylmethano)-1,2-benzoisothiazol-3(2H)-one 1,1-dioxide which can be reacted with sulfuryl chloride to give 2-chloromethyl-4,5,6,7-tetrahydro-4,7-ethano(or 4,7-dimethylmethano)-1,2-benzoisothiazol-3(2H)-one, i.e., 2-chloromethyl-4,5,6,7-tetrahydro-4,7-ethanosaccharin (Prep. 90) or 2-chloromethyl-4,5,6,7-tetrahydro-4,7-dimethylmethanosaccharin (Prep. 91).

PREPARATIONS 92E–94E

General procedure for the preparation of methyl 2-alkylcyclohexan-6-onecarboxylate To a suspension of anhydrous CuI (10 mmol) in anhydrous THF (100 mL) was added Me$_2$S (100 mmol) and the resulting solution was cooled to −78° C. The Grignard reagent (alkyl magnesium bromide) (20 mmol) was added over a period of 15 min. After being stirred at −78° C. for an hour, a solution of cyclohexenone (10 mmol) in THF was added and stirring continued for another 15 min. To the resulting mixture was added HMPA (5 mL) and, after 15 min, methyl cycloformate (30 mmol) in THF (20 mL) and the reaction warmed to room temperature and stirred overnight. The reaction mixture was quenched with 2N HCl (50 mL). The layers were separated and the aqueous phase extracted with Et$_2$O (1×100 mL). The combined organic extracts were washed with saturated NH$_4$Cl solution (3×50 mL), water (2×50 mL), brine (1×50 mL) and dried (Na$_2$SO$_4$). Removal of the solvent in vacuo and purification by either Kugelrohr distillation or flash chromatography afforded the desired methyl 2-alkylcyclohexan-6-onecarboxylate (TABLE C).

TABLE C

| Intermediate | Alkyl | Yield(%) | b.p. |
|---|---|---|---|
| 92A | Me | 82 | — |
| 93A | Et | 70 | 100–110° C. (0.2 mm) |
| 94A | i-Pr | 74 | 106–109° C. (0.5 mm) |

General procedure for the preparation of methyl 2-benzylthio-6-alkylcyclohex-2-enecarboxylate and methyl 2-benzylthio-6-alkylcyclohex-1-enecarboxylate A mixture of methyl 2-alkylcyclohexan-6-onecarboxylate (1 eq), benzylmercaptan (1.1 eq) and the acidic clay montmorillonite, KSF (1.5 times the weight of methyl 2-alkylcyclohexan-6-onecarboxylate) in anhydrous toluene (50–100 mL) was refluxed under nitrogen with azeotropic removal of water for 12–14 hr and cooled to room temperature. The solids were filtered off and washed with ether. The combined filtrate was washed with 10% Na$_2$CO$_3$, water, brine and dried. Removal of the solvent in vacuo and purification of the residue by flash chromatography on silica gel (10% ether in hexanes) gave a mixture of methyl 2-benzylthio-6-alkylcyclohex-2-enecarboxylate and methyl 2-benzylthio-6-alkylcyclohex-1-enecarboxylate (TABLE D) which was used in the next step as a mixture.

TABLE D

| Intermediate | Alkyl | Combined Yield of Mixture(%) |
|---|---|---|
| 92B | Me | 44 |
| 93B | Et | 50 |
| 94B | i-Pr | 52 |

General procedure for the preparation of 4-alkyltetrahydrosaccharin

A solution of methyl 2-benzylthio-6-alkylcyclohex-2-enecarboxylate and methyl 2-benzylthio-6-alkylcyclohex-1-enecarboxylate (1–10 mmol of the mixture) in 10 mL of MDC was diluted with 20–50 mL of glacial acetic acid and 1–5 mL of water, the mixture cooled to −10° C., and chlorine gas was bubbled through the mixture until the exothermic reaction subsided. The mixture was then stirred for 10 min and taken to dryness to give a mixture of methyl 2-chlorosulfonyl-6-alkylcyclohex-2-enecarboxylate and methyl 2-chlorosulfonyl-6-alkylcyclohex-1-enecarboxylate, which was dissolved in 10 mL of THF and added to 25 mL of a solution of concentrated ammonium hydroxide while cooling in an ice/acetone bath. After stirring for 2 hr, the reaction mixture was concentrated in vacuo, the residue taken up in water, acidified to pH 1 with 2N HCl, and extracted with MDC. The organic phase was dried and concentrated in vacuo to give a mixture of methyl 2-aminosulfonyl-6-alkylcyclohex-2-enecarboxylate and methyl 2-aminosulfonyl-6-alkylcyclohex-1-enecarboxylate.

The mixture was dissolved in methanol and added to a freshly prepared solution of sodium methoxide (10–50 mmol) and stirred at ambient temperature for 12 hr. The reaction mixture was concentrated in vacuo, diluted with water and extracted with ether. The organic phase was discarded, and the aqueous phase was acidified to pH 1 with concentrated HCl and extracted with MDC. The organic extracts, on washing with brine, drying and evaporation to dryness, afforded 4-alkyl-4,5,6,7-tetrahydro-1,2-benzisothiazol-3(2H)-one 1,1-dioxide (4-alkyl-4,5,6,7-tetrahydrosaccharin) (TABLE E).

TABLE E

| Intermediate | Alkyl | Yield(%) |
|---|---|---|
| 92C | Me | 85 |
| 93C | Et | 80 |
| 94C | i-Pr | 74 |

A mixture of 4-alkyl-4,5,6,7-tetrahydro-1,2-benzisothiazol-3(2H)-one 1,1-dioxide (4-alkyl-4,5,6,7-tetrahydrosaccharin) (1.0 eq), chloromethyl phenyl sulfide (1.5 eq) and tetrabutylammonium bromide (0.2 eq) in toluene (25 mL/g of saccharin) was refluxed under nitrogen for 16–24 hr and then cooled to room temperature. The resulting mixture was evaporated to dryness and the residue chromatographed on silica gel eluting with hexanes/MDC (1:1 to 1:3) to give the corresponding 2-phenylthiomethyl-4-alkyl-4,5,6,7-tetrahydro-1,2-benzisothiazol-3(2H)-one 1,1-dioxide (2-phenylthiomethyl-4-alkyl-4,5,6,7-tetrahydrosaccharin) (TABLE F).

TABLE F

| Intermediate | Alkyl | Yield(%) |
|---|---|---|
| 92D | Me | 55 |
| 93D | Et | 40 |
| 94D | i-Pr | 53 |

A solution of 2-phenylthiomethyl-4-alkyl-4,5,6,7-tetrahydrosaccharin (1.0 eq) was treated with sulfuryl chloride (1.5 eq) and stirred for 2 hr. The resulting yellow solution was taken to dryness to give the 2-chloromethyl-4-alkyl-4,5,6,7-tetrahydrosaccharin. The compounds prepared are those wherein alkyl is Me (92E), Et (93E) and i-Pr (94E).

PREPARATION 95

By following the general procedure described for Preparations 92B-94B to 92E-94E and starting with methyl cyclohexan-6-onecarboxylate, there was obtained, successively, a mixture of methyl 2-benzylthiocyclohex-1(and 2)-enecarboxylate (40% yield), a mixture of methyl 2-chlorosulfonylcyclohex-1(and 2)-enecarboxylate, a mixture of methyl 2-aminosulfonylcyclohex-1(and 2)-enecarboxylate, 4,5,6,7-tetrahydro-1,2-benzisothiazol-3(2H)-one 1,1-dioxide (4,5,6,7-tetrahydrosaccharin) (50% yield), 2-phenylthiomethyl-4,5,6,7-tetrahydro-1,2-benzisothiazol-3(2H)-one 1,1-dioxide (2-phenylthiomethyl-4,5,6,7-tetrahydrosaccharin) (40% yield) and 2-chloromethyl-4,5,6,7-tetrahydro-1,2-benzisothiazol-3(2H)-one 1,1-dioxide (2-chloromethyl-4,5,6,7-tetrahydrosaccharin).

PREPARATION 96

Methyl 2,2-dimethylcyclohexan-6-one carboxylate

To a suspension of anhydrous CuI (70.0 g, 0.37 mol) in anhydrous ether (500 mL) at 0° C. was added halide-free methyl lithium (520 mL or 1.4M solution in ether, 0.73 mol). After being stirred at 0° C. for 15 min, a solution of 3-methyl-2-cyclohexenone (20.0 g, 0.18 mol) in ether (50 mL) was added and stirring continued for another 1 hr. To the resulting mixture was added THF (50 mL) and HMPA (25 mL) and after 15 min methyl cyanoformate (45.0 g, 0.53 mol) in THF (20 mL) and the reaction warmed to room temperature and stirred for 3 hr. The reaction mixture was quenched with 2N HCl (50 mL). The layers were separated and the aqueous phase extracted with Et$_2$O (1×500 mL). The combined organic extracts were washed with saturated NH$_4$Cl solution (3×50 mL), water (2×50 mL), brine (1×50 mL) and dried (Na$_2$SO$_4$). Removal of the solvent in vacuo and purification by Kugelrohr distillation afforded 34.0 g (99%) of methyl 2,2-dimethylcyclohexan-6-one carboxylate, bp 80°-84° C./0.6 mm, which was converted to 2-chloromethyl-4,4-dimethyl-4,5,6,7-tetrahydrosaccharin following the general procedures described above for Preparations 92B-94B to 92E-94E.

PREPARATION OF THE FINAL PRODUCTS

EXAMPLE 1

A solution of 2-bromomethylsaccharin (2.0 g, 7.2 mmol), dibutyl phosphate (2.29 g, 10.9 mmol) and N,N-diisopropylethylamine (1.41 g, 10.9 mmol) in 40 mL of methylene chloride was stirred at room temperature for 48 hr. The reaction mixture was concentrated and the residue flash chromatographed on silica gel eluting with 30% ethyl acetate in hexanes to give 2.35 g (80%) of dibutyl 2-saccharinylmethyl phosphate as a colorless oil.

EXAMPLE 2

A solution of 2-chloromethyl-4-ethoxysaccharin (2.0 g, 7.3 mmol), diethyl phosphate (1.68 g, 10.9 mmol), and triethylamine (1.53 mL, 10.9 mmol) in 25 mL of methylene chloride was refluxed for 58 hr. On cooling, the reaction mixture was concentrated and the residue flash chromatographed on silica gel eluting with ethyl acetate-hexanes to give 2.0 g (73%) of diethyl 4-ethoxy-2-saccharinylmethyl phosphate as a colorless oil.

EXAMPLE 3

To a solution of dibenzyl phosphate (0.69 g, 2.48 mmol) in 30 mL of methanol at room temperature was added cesium carbonate (0.403 g, 1.24 mmol). After stirring for 2 hr, the solvent was evaporated and the residue was dried under high vacuum and suspended in 10 mL of N,N-dimethylformamide. To the suspension was added 2-chloromethyl-4-isopropyl-6-methoxysaccharin (0.5 g, 1.6 mmol) and the mixture stirred at 50° C. in an oil bath for 24 hr. On cooling, the mixture was diluted with ice-water and extracted with 200 mL of ether-ethyl acetate (4:1). The organic layer was separated and washed successively with water and then saturated brine. The extract was dried over magnesium sulfate, filtered, concentrated, and the residue was flash chromatographed on silica gel eluting with ethyl acetate-hexanes to give 0.46 g (52%) of dibenzyl 4-isopropyl-6-methoxy-2-saccharinylmethyl phosphate as an oil which crystallized on standing, mp 75.5°-76.5° C.

Following procedures similar to those described in Examples 1, 2 and 3 above (Methods 1, 2 and 3 respectively hereafter), the compounds of Formula I listed in TABLE 1 below were similarly prepared. In each of Examples 4-9 the products were prepared from 2-bromomethylsaccharin. In Examples 10-21 the products were prepared from the corresponding 2-chloromethylsaccharin.

TABLE 1

| Example | R$_1$ | R$_2$/R$_3$ | m = n = | A = B = | Method | mp(°C.) | Yield(%) |
|---|---|---|---|---|---|---|---|
| 4 | H | H/H | 1 | CH$_2$Ph | 1 | oil | 39 |
| 5 | H | H/H | 1 | CH$_3$ | 1 | oil | 20 |
| 6 | H | H/H | 1 | CH$_2$CH$_3$ | 1 | oil | 71 |
| 7 | H | H/H | 1 | Ph | 1 | oil | 24 |
| 8 | H | H/H | 0 | Ph | 1 | 128.5-129.5 | 75 |
| 9 | H | H/H | 0 | C$_6$H$_4$-4-(OCH$_3$) | 1 | foam | 88 |
| 10 | CH(CH$_3$)$_2$ | H/H | 1 | CH$_2$CH$_3$ | 2 | oil | 83 |
| 11 | OCH$_3$ | 6-OCH$_3$/H | 1 | CH$_2$CH$_3$ | 2 | 110.0-111.0 | 63 |
| 12 | CH(CH$_3$)(CH$_2$CH$_3$) | H/H | 1 | CH$_2$CH$_3$ | 2 | oil | 25 |
| 13 | CH(CH$_3$)$_2$ | 6-OCH$_3$/H | 1 | CH$_2$CH$_3$ | 2 | oil | 66 |
| 14 | CH(CH$_3$)$_2$ | H/H | 0 | Ph | 2 | 137.5-138.5 | 53 |
| 15 | CH(CH$_3$)$_2$ | 6-OCH$_3$/H | 0 | Ph | 2 | foam | 78 |
| 16 | CH(CH$_3$)$_2$ | H/H | 1 | CH$_2$Ph | 1 | oil | 37 |
| 17 | CH(CH$_3$)$_2$ | 6-OH/H | 1 | CH$_2$CH$_3$ | 3 | 127.5-128.5 | 23 |
| 18 | CH(CH$_3$)$_2$ | 6-OCH$_3$/H | 1 | CH(CH$_3$)$_2$ | 3 | 101.5-102.5 | 57 |
| 19 | CH(CH$_3$)$_2$ | 6-OCH$_2$CH$_3$/H | 1 | CH(CH$_3$)$_2$ | 3 | 96.0-97.0 | 66 |
| 20 | CH(CH$_3$)$_2$ | 6-OCH$_3$/H | 0 | (CH$_2$)$_3$CH$_3$ | 3 | oil | 52 |

TABLE 1-continued

| Example | R$_1$ | R$_2$/R$_3$ | m = n = | A = B = | Method | mp(°C.) | Yield(%) |
|---|---|---|---|---|---|---|---|
| 21 | CH(CH$_3$)$_2$ | 6-OH/H | 1 | CH(CH$_3$)$_2$ | 3 | 123-125 | 58 |

The phosphate and phosphinic acid starting materials employed in the preparation of the compounds of Examples 1-17 and 20 are commercially available. Diisopropyl phosphate used in Examples 18, 19 and 21 was prepared as follows:

A mixture of diisopropyl chlorophosphate (10 g, 50 mmol) (reference: R. A. McIvor et al., *Can. J. Chem.* 34, 1819 (1956)) in 100 mL of distilled water was stirred at 80° C. in an oil bath for 2 hr. The mixture was concentrated under vaccum and the residual water was removed by azeotropic distillation with benzene (3×100 ml). After drying under high vacuum, 8.8 g (97%) of diisopropyl phosphate was obtained as an oil and used without purification.

EXAMPLE 22

Diisopropyl 6-(2,2-dimethyl-1,3-dioxolan-4-yl)methoxy-4-isopropyl-2-saccharinylmethyl phosphate Diethyl azodicarboxylate (0.96 g, 5.55 mmol) was added to a mixture of diisopropyl 6-hydroxy-4-isopropyl-2-saccharinylmethyl phosphate (2.37 g, 5.44 mmol), triphenylphosphine (1.44 g, 5.5 mmol) and glycerol dimethylketal (2,2-dimethyl-1,3-dioxolane-4-methanol) (0.79 g, 5.98 mmol) in 40 mL of THF and the mixture was stirred for 15 hr at RT. Excess solvent was removed under reduced pressure and the residue was flash chromatographed (SiO$_2$; ethyl acetate-MDC) to give a first fraction yielding 0.49 g (19.7%) of the title compound as a thick oil, and a second fraction yielding 2.0 g of a mixture containing about 85% of the title compound.

EXAMPLE 23

2-Saccharinylmethyl phosphate

Dibenzyl 2-saccharinylmethyl phosphate (1.1 g), dissolved in 50 ml methanol, was subjected to hydrogenation over 10% Pd-C (0.3 g) at normal pressure for approximately 6 hr. The solution was concentrated under reduced pressure to give 2-saccharinylmethyl phosphate as a thick oily residue which was dissolved in methanol and treated with cyclohexylamine (0.59 mL). On standing at RT crystals of the salt separated which were collected by filtration, washed with methanol-ether and dried to give 0.503 g (43.9%) of the dicyclohexylamine salt of the title compound; mp (shrinks at 214°-215° C.).

EXAMPLE 24 a) Methyl 2,2-dimethylcyclohexan-6-onecarboxylate

To a suspension of anhydrous CuI (70.0 g, 0.37 mol) in anhydrous ether (500 mL) at 0° C. was added halide-free methyl lithium (520 mL of 1.4M solution in ether, 0.73 mol). After being stirred at 0° C. for 15 min, a solution of 3-methyl-2-cyclohexen-1-one (20.0 g, 0.18 mol) in ether (50 mL) was added and stirring was continued for 1 hr. To the resulting mixture was added THF (50 mL) and HMPA (25 mL) and after 15 min methyl cyanoformate (45.0 g, 0.53 mol) in THF (20 mL) and the reaction warmed to room temperature and stirred for 3 hr. The reaction mixture was quenched with 2N HCl (50 mL). The layers were separated and the aqueous phase extracted with Et$_2$O (1×500 mL). The combined organic extracts were washed with saturated NH$_4$Cl solution (3×50 mL), H$_2$O (2×50 mL), brine (1×50 mL) and dried (Na$_2$SO$_4$). Removal of the solvent in vacuo and purification by Kugelrohr distillation afforded 34.0 g (99%) of methyl 2,2-dimethylcyclohexan-6-onecarboxylate, b.p.$_{0.6}$ 80°-84° C.

b) Methyl 2-benzylthio-6,6-dimethylcyclohex-2-enecarboxylate and methyl 2-benzylthio-6,6-dimethylcyclohex-1-enecarboxylate Amberlyst-15 acidic resin (25.0 g) was mixed with polyphosphoric acid (3.0 g) and phosphoric acid (3.0 g) and heated under vacuum at 60° C. for 2 hr. The resulting resin was mixed with methyl 2,2-dimethylcyclohexan-6-onecarboxylate (34.0 g, 0.18 mol), benzyl mercaptan (50.0 g, 0.40 mol) and powdered sieves 4 Å (20.0 ) in anhydrous dichloroethane (700 mL) and heated at reflux under nitrogen for 18 hr and cooled to room temperature. The solids were filtered off, the filtrate concentrated in vacuo and excess benzyl mercaptan distilled off. The pot residue was purified by chromatography (2:1/MDC:hexanes) to give 11.3 g (21%) of a mixture of methyl 2-benzylthio-6,6-dimethylcyclohexen-2-enecarboxylate and methyl 2-benzylthio-6,6-dimethylcyclohex-1-enecarboxylate.

c) The latter mixture (11.3 g, 0.04 mol) was dissolved in MDC (25 mL), diluted with glacial acetic acid (65 mL), water (10 mL), cooled to −10° C., and chlorine gas was bubbled through the mixture until the exothermic reaction subsided. The mixture was then stirred for 10 min and taken to dryness to give a mixture of methyl 2-chlorosulfonyl-6,6-dimethylcyclohexen-2-enecarboxylate and methyl 2-chlorosulfonyl-6,6-dimethylcyclohex-1-enecarboxylate, which was dissolved in 10 mL of THF and added to 25 mL of a solution of conc. ammonium hydroxide while cooling in an ice/acetone bath. After stirring for 2 hr, the reaction mixture was concentrated in vacuo, the residue taken up in water, acidified to pH 1 with 2N HCl, and extracted with MDC. The organic phase was dried and concentrated in vacuo to give a mixture of methyl 2-aminosulfonyl-6,6-dimethylcyclohex-2-enecarboxylate and methyl 2-aminosulfonyl-6,6-dimethylcyclohex-1-enecarboxylate. The latter mixture was dissolved in methanol (25 mL) and added to a freshly prepared solution of sodium methoxide (0.20 mol) and stirred at ambient temperature for 12 hr. The reaction mixture was concentrated in vacuo, diluted with water and extracted with ether. The organic phase was discarded, and the aqueous phase acidified to pH 1 with concentrated HCl and extracted with MDC. The organic extracts, on washing with brine, drying and evaporation to dryness, afforded 3.5 g (42%) of 4,4-dimethyl-4,5,6,7-tetrahydro-1,2-benzisothiazol-3(2H)-one 1,1-dioxide (4,4-dimethyl-4,5,6,7-tetrahydrosaccharin).

d) A mixture of 4,4-dimethyl-4,5,6,7-tetrahydrobenzisothiazol-3(2H)-one 1,1-dioxide (1.0 g, 4.7 mmol), chloromethyl phenyl sulfide (1.1 g, 7.0 mmol) and tetrabutyl ammonium bromide (0.3 g, 0.93 mmol) in toluene (25 mL) was refluxed under nitrogen for 16-24 hr and then cooled to room temperature. The resulting mixture was evaporated to dryness and the residue chromatographed on silica gel eluting with hexanes/MDC (1:1 to 1:3) to give 1.0 g (67%) of 2-phenyl-thiomethyl-4,4-dimethyl-4,5,6,7-tetrahydro-1,2-benziso-thiazol-3(2H)-one 1,1-dioxide (2-phenylthiomethyl-4,4-dimethyl-4,5,6,7-tetrahydrosaccharin).

e) A solution of 2-phenylthiomethyl-4,4-dimethyl-4,5,6,7-tetrahydrobenzisothiazol-3(2H)-one 1,1-dioxide (0.8 g, 2.4 mmol) was treated with sulfuryl chloride (0.48 g, 3.5 mmol) and stirred for 2 hr. The resulting yellow solution was taken to dryness, diluted with ether (100 mL) and washed with saturated NaHCO$_3$ and brine. The organic phase was dried and concentrated in vacuo to give 0.6 g (95%) of 2-chloromethyl-4,4-dimethyl-4,5,6,7-tetrahydro-1,2-benzisothiazol-3(2H)-one 1,1-dioxide (2-chloromethyl-4,4-dimethyl-4,5,6,7-tetrahydrosaccharin), which was treated with diethyl phosphate (1.05 g, 6.8 mmol) and triethylamine (0.7 g, 6.9 mmol) in dichloroethane (15 mL) at 50° C. for 16 hr and cooled to room temperature. The resulting mixture was taken to dryness and purified by flash chromatography on silica gel (40% hexanes in ethyl acetate) to give 0.18 g (21%) of diethyl 4,4-dimethyl-4,5,6,7-tetrahydro-3-oxobenzisothiazolin-2-ylmethyl 1,1-dioxide phosphate (diethyl 4,4-dimethyl-4,5,6,7-tetrahydro-2-saccharinylmethyl phosphate) as a colorless oil.

EXAMPLE 25

Diisopropyl 6-ethoxy-4-isopropyl-2-saccharinylmethyl phosphate (Example 19) can also be prepared by a procedure similar to that of Example 22, i.e., by reacting diisopropyl 6-hydroxy-4-isopropyl-2-saccharinylmethyl phosphate with triphenylphosphine, ethanol and diethyl azodicarboxylate.

Following the procedure of Example 22 but substituting for glycerol dimethylketal the appropriate alcohol, there can be prepared the diisopropyl 4-R$_1$-R$_2$-R$_3$-2-saccharinylmethyl phosphates in TABLE 2.

TABLE 2

| Example | R$_1$ | R$_2$ | R$_3$ |
|---|---|---|---|
| 26 | CH(CH$_3$)$_2$ | 6-OCH$_2$(CH$_3$)$_2$ | H |
| 27 | CH(CH$_3$)$_2$ | 6-(OCH$_2$CH$_2$)$_2$OCH$_3$ | H |
| 28 | CH(CH$_3$)$_2$ | 6-OCH$_2$COOCH$_3$ | H |
| 29 | CH(CH$_3$)$_2$ | 6-OCH$_2$CH$_2$(OCH$_3$)CH$_2$OCH$_3$ | H |
| 30 | CH(CH$_3$)$_2$ | 6-O-cyclobutyl | H |
| 31 | CH(CH$_3$)$_2$ | 6-OP(O)(OCH$_2$CH$_3$)$_2$ | H |
| 32 | CH(CH$_3$)$_2$ | 6-OCH$_2$CH$_2$-1-morpholinyl | H |

The 2,3-dimethoxy-1-propanol which is used in the preparation of Example 29 was synthesized as follows:

A solution of 10.0 g (0.055 mol) of DL-α-O-benzylglycerol in a little THF was added to a suspension of 15.38 g (0.137 mol) of potassium tert-butoxide in 300 mL of THF. The mixture was stirred for 1 hr at RT and 18.72 g (0.132 mol) of iodomethane was added. A white solid immediately separated. The reaction was stirred for 10 hr at RT, cooled, carefully diluted with sodium chloride solution and extracted with ether. The organic layer was washed with water, 5% HCl, water and saturated NaCl and dried. The solvent was removed and the residue was purified by flash chromatography to give 1-benzyloxy-2,3-dimethoxypropane, 9.16 g (79%), as an oil.

A solution of 8.8 g (0.042 mol) of this material in 200 ml of MeOH was hydrogenated using 1.1 g of 10% Pd/C at 50 psi. The catalyst was removed by filtration and the solvent was evaporated under reduced pressure to give 4.4 g (87%) of 2,3-dimethoxy-1-propanol.

EXAMPLE 33

By reacting diisopropyl 6-hydroxy-4-isopropyl-2-saccharinylmethyl phosphate (1 mol) in MDC, with trifluoromethanesulfonic anhydride (1.3 mol) in the presence of triethylamine (3 mol) at 0° C. there can be obtained, after standard workup and purification, diisopropyl 4-isopropyl-6-trifluoromethanesulfonyloxy-2-saccharinylmethyl phosphate.

EXAMPLE 34

By reacting in a nitrogen atmosphere the product of Example 33 (1 mol), in p-dioxane, with 1-methyl-2-trimethylstannyl-pyrrole (1.6 mol) in the presnce of tetrakis (triphenylphosphine) palladium (O) (0.02 mol), lithium chloride (3.1 mol) and 2,6-di-tert-butyl-4-methylphenol (0.1 mol) under reflux, there can be obtained, after standard workup and purification, diisopropyl 4-isopropyl-6-[2-(1-methylpyrrolyl)]-2-saccharinylmethyl phosphate.

EXAMPLE 35

By reacting the product of Example 33 (1 mol) in THF with 40% aqueous dimethylamine (4.4 mol) at RT, there can be obtained after standard workup and purification, diisopropyl 6-dimethylamino-4-isopropyl-2-saccharinylmethyl phosphate.

EXAMPLE 36

By reacting diisopropyl 6-hydroxy-4-isopropyl-2-saccharinylmethyl phosphate in toluene with di-(sec-butoxymethyl)methylamine at 80° C., there can be obtained, after standard workup and purification, phosphoric acid diisopropyl 4-isopropyl-8-methyl-2,3,7,8-tetrahydro-9H-1,3-oxazino-[6,5-g]-3-oxobenzisothiazol-2-ylmethyl 1,1-dioxide ester.

EXAMPLE 37

By treating diisopropyl 6-(2,2-dimethyl-1,3-dioxolan-4-yl)methoxy-4-isopropyl-2-saccharinylmethyl phosphate (Example 22) (1 mol) with p-toluenesulfonic acid monohydrate (0.8 mol) in methanol-chloroform at RT, there can be obtained, after standard workup and purification, diisopropyl 6-(2,3-dihydroxypropoxy)-4-isopropyl-2-saccharinylmethyl phosphate.

EXAMPLE 38

By reacting diisopropyl 6-hydroxy-4-isopropyl-2-saccharinylmethyl phosphate (1 mol) in acetone with tert-butyl bromoacetate (3.4 mmol) in the presence of anhydrous potassium carbonate (1.96 mol) at RT, there can be obtained, after standard workup and purification, diisopropyl 6-(2-tertbutoxy-2-oxoethoxy)-4-isopropyl-2-saccharinylmethyl phosphate.

EXAMPLE 39

By substituting benzyl bromoacetate for tert-butyl bromoacetate in Example 38, there can be obtained diisopropyl 6-(2-benzyloxy-2-oxoethoxy)-4-isopropyl-2-saccharinylmethyl phosphate which can be converted by hydrogenation over palladium-on-carbon to diisopropyl 6-carboxymethoxy-4-isopropyl-2-saccharinylmethyl phosphate.

EXAMPLE 40

Following the procedure of Example 3 but substituting 2-chloromethyl-4-hydroxysaccharin for 2-chloromethyl-4-isopropyl-6-methoxysaccharin there can be obtained dibenzyl 4-hydroxy-2-saccharinylmethyl phosphate.

EXAMPLE 41

Following a procedure similar to that of Example 22, dibenzyl 4-hydroxy-2-saccharinylmethyl phosphate can be reacted with diethyl diazocarboxylate, triphenylphosphine and benzyl alcohol to give dibenzyl 4-benzyloxy-2-saccharinylmethyl phosphate.

Following a procedure similar to that described in Example 3, each of the 4-$R_1$-$R_2$-$R_3$-2-chloromethylsaccharins of Preparations 1 to 86, the 4-$R_4$-4-$R_5$-6-$R_6$-chloromethyl-4,5,6,7-tetrahydrosaccharins of Preparations 87, 88, 92E to 94E, 95 and 96 and the 4,7-methano-, 4,7-dimethylmethano- and 4,7-ethano-4,5,6,7-tetrahydrosaccharins of Preparations 89 to 91 respectively can be reacted with each of the phosphoric acid di-esters, phosphonic acid mono-esters and phosphinic acids of formula III listed in TABLES 3 and 4 to give the corresponding compounds of formulas I, II and IIA respectively.

TABLE 3

| | Formula III | |
|---|---|---|
| m/n | A | B |
| 1/1 | CH₂CH₂CH₂CH₂CH₂<br>\|<br>CH₂CH₃ | CH₂CH₂CH₂CH₂CH₂<br>\|<br>CH₂CH₃ |
| 1/1 | CH₂(CH₂)₈CH₃ | CH₂(CH₂)₈CH₃ |
| 1/1 | C₆H₄-4-(OCH₃) | C₆H₄-4-(OCH₃) |
| 0/1 | Ph | CH₂Ph |
| 0/1 | Ph | 2-pyridyl |
| 0/1 | CH₂CH(CH₃)₂ | CH₃ |
| 0/1 | Ph | CH₃ |
| 0/1 | CH₃ | CH₃ |
| 0/1 | CH₃ | CH₂CH₃ |
| 0/0 | Ph | CH₂CH₃ |
| 0/0 | Ph | CH₂(CH₃)₂ |
| 0/0 | Ph | CH₂Ph |
| 0/0 | CH₃ | CH₃ |
| 0/0 | CH₂CH₃ | CH₂CH₃ |
| 0/0 | CH₃(CH₂)₈CH₂ | CH₃(CH₂)₈CH₂ |

TABLE 4

Formula III: m = n = 1; A and B taken together

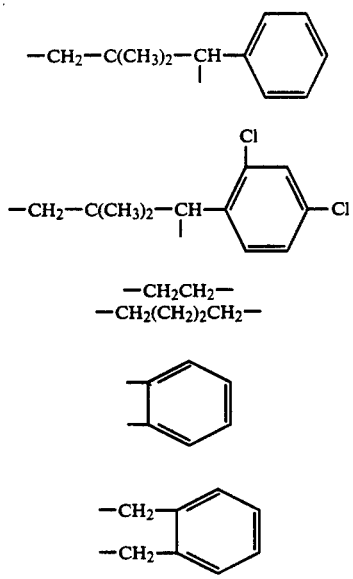

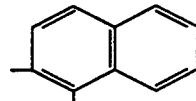

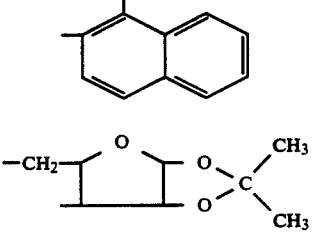

TABLE 4-continued

Formula III: m = n = 1; A and B taken together

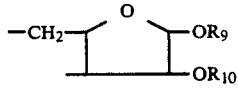

The methylphosphonic acid mono(2-methylpropyl) ester and methylphosphonic acid monophenyl ester in TABLE 3 can be prepared from methylphosphonochloridic acid (2-methylpropyl) ester and methylphosphonochloridic acid phenyl ester respectively by hydrolysis.

The ethylphenylphosphinic acid and isopropylphenylphosphinic acid in TABLE 3 can be prepared by conventional O-alkyl cleavage from the corresponding methyl esters, e.g., by reaction with trimethylsilyl bromide [(CH₃)₃SiBr] and hydrolysis of the trimethylsilyl ester so formed.

Conventional hydrolysis under acidic conditions of the compound resulting in each case from reaction of the chloromethyl compounds of Preparations 1 to 96 with the compound of formula III wherein A and B together represent $$-CH_2 \overbrace{\phantom{XXXX}}^{O} OR_9$$
$$\phantom{-CH_2XXXXX} OR_{10}$$

wherein $R_9$ and $R_{10}$ together represent isopropylidene (TABLE 4) affords the corresponding compound wherein $R_9$ and $R_{10}$ each is hydrogen.

BIOLOGICAL TEST RESULTS

Measurement of the inhibition constant, $K_i$, of a HLE-inhibitor complex has been described for "truly reversible inhibition constants" usually concerning competitive inhibitors [Cha, Biochem. Pharmacol., 24, 2177-2185 (1975)]. The compounds of the present invention, however, do not form truly reversible inhibitor complexes but are consumed by the enzyme to some extent. Thus, instead of measuring a $K_i$, a $K_i^*$ is calculated which is defined as the ratio of the $k_{off}/k_{on}$, the rate of reactivation of the enzyme to the rate of inactivation of the enzyme. The values of $k_{off}$ and $k_{on}$ are measured and $K_i^*$ is then calculated.

The rate of inactivation, $k_{on}$, of enzymatic activity was determined for the compounds tested by measuring the enzyme activity of an aliquot of the respective enzyme as a function of time after addition of the test compound. By plotting the log of the enzyme activity against time, an observed rate of inactivation, $k_{obs}$, is obtained which can be represented as $k_{obs} = \ln 2/t_{\frac{1}{2}}$ where $t_{\frac{1}{2}}$ is the time required for the enzyme activity to drop by 50%. The rate of inactivation is then equal to $$k_{on} = \frac{k_{obs}}{[I]}$$

where [I] is the concentration of the inhibiting compound.

The reactivation constant, $k_{off}$, is similarly determined, and the inhibition constant, $K_i^*$, is then calculated as $$K_i^* = k_{off}/k_{on}.$$

The $K_i^*$ values determined for the compounds of Examples 1 to 22 were in the range of from 0.035 to 100 nM.

The compound of Example 13 had a $K_i^*$ of 0.035.

We claim:

1. A compound having the formula:

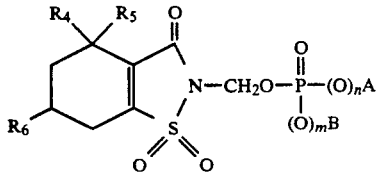

wherein:

$R_4$ is hydrogen, lower-alkyl or phenyl;

$R_5$ is hydrogen or primary lower-alkyl;

or $R_4$ and $R_5$, taken together, represent ethylene;

$R_6$ is hydrogen or lower-alkoxy;

m and n are independently 0 or 1;

when m and n are 1, A and B are independently hydrogen, lower-alkyl, phenyl or benzyl, or, taken together, represent:

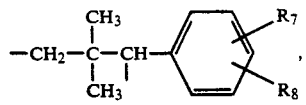

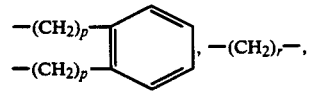

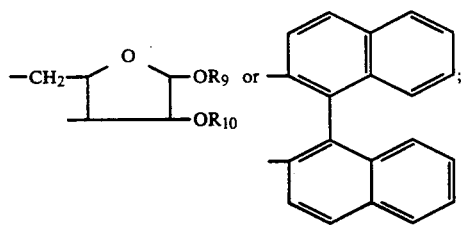

where $R_7$ and $R_8$ are independently hydrogen or chlorine, $R_9$ and $R_{10}$ each is hydrogen or together represent isopropylidene, p is 0 or 1 and r is 2, 3 or 4;

when m is 1 and n is 0, A and B are independently lower-alkyl, phenyl, benzyl or 2-pyridinyl; and when m and n are 0, A and B are independently lower-alkyl, phenyl or phenyl substituted by lower-alkoxy; or acid-addition salts of basic members or base-addition salts of acidic members thereof.

2. A compound according to claim 1 wherein:
$R_4$ is hydrogen or lower-alkyl; and
$R_5$ is hydrogen or primary lower-alkyl;
or $R_4$ and $R_5$, taken together, represent ethylene.

3. A compound according to claim 2 wherein:
$R_4$ is hydrogen or $C_{1-3}$-lower-alkyl; and
$R_5$ is hydrogen or $C_{1-3}$-primary lower-alkyl;
or $R_4$ and $R_5$, taken together, represent ethylene.

4. A compound according to claim 3 wherein:
$R_4$ is hydrogen, methyl, ethyl or isopropyl;
$R_5$ is hydrogen or methyl;
$R_6$ is hydrogen or methoxy;
m and n are 1; and
A and B are lower-alkyl.

5. Diethyl 4,4-dimethyl-4,5,6,7-tetrahydro-2-saccharinylmethyl phosphate according to claim 4.

6. A composition for the treatment of degenerative diseases which comprises a pharmaceutical carrier and an effective proteolytic enzyme inhibiting amount of a compound according to claim 1.

7. A composition for the treatment of degenerative diseases which comprises a pharmaceutical carrier and an effective proteolytic enzyme inhibiting amount of a compound according to claim 4.

8. A method for the treatment of degenerative diseases which comprises administering to a patient in need of said treatment a medicament containing an effective proteolytic enzyme inhibiting amount of a compound according to claim 1.

9. A method for the treatment of degenerative diseases which comprises administering to a patient in need of said treatment a medicament containing an effective proteolytic enzyme inhibiting amount of a compound according to claim 4.

* * * * *

UNITED STATES PATENT AND TRADEMARK OFFICE
CERTIFICATE OF CORRECTION

PATENT NO. : 5,187,173

DATED : February 16, 1993

INVENTOR(S) : Ranjit C. Desai and Chakrapani Subramanyan

It is certified that error appears in the above-identified patent and that said Letters Patent is hereby corrected as shown below:

On the title page, in item [75]:
In the names of the inventors, delete "; John J. Court" and "both" and delete "Dennis J. Hlasta, Clifton Park;"

Signed and Sealed this

Twenty-sixth Day of July, 1994

Attest:

BRUCE LEHMAN

Attesting Officer

Commissioner of Patents and Trademarks